(12) United States Patent
Hancock et al.

(10) Patent No.: US 11,832,881 B2
(45) Date of Patent: Dec. 5, 2023

(54) ELECTROSURGICAL INSTRUMENT WITH IMPEDANCE TRANSFORMER FOR DELIVERING MICROWAVE ENERGY

(71) Applicant: CREO MEDICAL LIMITED, Chepstow (GB)

(72) Inventors: Christopher Paul Hancock, Bath (GB); Malcolm White, Chepstow (GB); Patrick Burn, Chepstow (GB)

(73) Assignee: CREO MEDICAL LIMITED, Chepstow (GB)

( * ) Notice: Subject to any disclaimer, the term of this patent is extended or adjusted under 35 U.S.C. 154(b) by 229 days.

(21) Appl. No.: 17/371,579

(22) Filed: Jul. 9, 2021

(65) Prior Publication Data
US 2021/0330381 A1    Oct. 28, 2021

Related U.S. Application Data

(62) Division of application No. 15/580,152, filed as application No. PCT/GB2016/051817 on Jun. 17, 2016, now Pat. No. 11,083,522.

(30) Foreign Application Priority Data

Jun. 19, 2015    (GB) .................................... 1510787

(51) Int. Cl.
    *A61B 18/18*    (2006.01)
    *A61B 18/12*    (2006.01)
    *A61B 18/00*    (2006.01)

(52) U.S. Cl.
CPC .......... *A61B 18/1815* (2013.01); *A61B 18/12* (2013.01); *A61B 2018/00077* (2013.01);
(Continued)

(58) Field of Classification Search
CPC ................ A61B 18/18; A61B 18/1815; A61B 2018/1861; A61B 2018/1869; A61B 2018/1884; A61B 2018/1892
See application file for complete search history.

(56) References Cited

U.S. PATENT DOCUMENTS 5,057,106 A * 10/1991 Kasevich ........... A61B 18/1815
                                                  600/549
5,843,144 A    12/1998 Rudie et al.
(Continued)

FOREIGN PATENT DOCUMENTS

CN        102473997 A    5/2012
WO    WO2004/047659 A2    6/2004
(Continued)

OTHER PUBLICATIONS

British Search Report of related British Patent Application No. GB1510787.3 dated Dec. 22, 2015.
(Continued)

*Primary Examiner* — Ronald Hupczey, Jr.
(74) *Attorney, Agent, or Firm* — ArentFox Schiff LLP

(57) ABSTRACT

An electrosurgical instrument for delivering microwave energy having a predetermined frequency into biological tissue in contact with the instrument, wherein the instrument comprises a first coaxial transmission line having a second coaxial transmission line connected to the distal end thereof, the second coaxial transmission line having a length and a characteristic impedance that are configured to match the impedance of the first coaxial transmission line to the load impedance at the distal end of the distal coaxial transmission line when the instrument is in contact with the tissue, at the operating frequency.

17 Claims, 11 Drawing Sheets

(52) U.S. Cl.
CPC .............. *A61B 2018/00529* (2013.01); *A61B 2018/00577* (2013.01); *A61B 2018/00589* (2013.01); *A61B 2018/00642* (2013.01); *A61B 2018/00732* (2013.01); *A61B 2018/00875* (2013.01); *A61B 2018/1823* (2013.01); *A61B 2018/1861* (2013.01)

(56) References Cited

U.S. PATENT DOCUMENTS

| | | |
|---|---|---|
| 6,224,593 B1 | 5/2001 | Ryan et al. |
| 8,998,891 B2 | 4/2015 | Garito et al. |
| 2003/0014043 A1 | 1/2003 | Henry et al. |
| 2010/0228244 A1 | 9/2010 | Hancock et al. |
| 2012/0172865 A1* | 7/2012 | Hancock ............ A61B 18/1815 606/33 |
| 2014/0194865 A1 | 7/2014 | Tani et al. |
| 2014/0290830 A1 | 10/2014 | Brannan |

FOREIGN PATENT DOCUMENTS

| | | |
|---|---|---|
| WO | WO2008/043999 A2 | 4/2008 |
| WO | WO 2014/049332 A1 | 4/2014 |

OTHER PUBLICATIONS

Communication from the State Intellectual Property Office of People's Republic of China in counterpart Application No. 201680034527.3, dated Nov. 19, 2019.

International Search Report and Written Opinion of related International Patent Application No. PCT/GB2016/051817 dated Nov. 10, 2016.

* cited by examiner

ELECTROSURGICAL INSTRUMENT WITH IMPEDANCE TRANSFORMER FOR DELIVERING MICROWAVE ENERGY

CROSS-REFERENCE TO RELATED APPLICATIONS

This application is a Divisional of U.S. patent application Ser. No. 15/580,152, filed on Dec. 6, 2017, now U.S. Pat. No. 11,083,522, which is a National Stage Entry of International Patent Application No. PCT/GB2016/051817, filed Jun. 17, 2016, which claims priority to United Kingdom Patent Application No. 1510787.3, filed Jun. 19, 2015. The disclosures of the priority applications are incorporated in their entirety by reference herein.

FIELD OF THE INVENTION

The present invention relates to an electrosurgical instrument for delivering microwave frequency energy into tissue in contact with the instrument. The present invention also relates to a method of manufacturing such an instrument.

A principle use of the electrosurgical instrument may be for haemostasis, in which case the device may be used to pre-coagulate vessels or to coagulate vessels once a bleed has occurred. The device may be mainly intended for use in the GI tract, but may also, or alternatively, be used in other parts of the body. The device may also, or alternatively, be used to ablate lesions, and may be particularly useful for ablation of lesions that are on the surface of an organ.

BACKGROUND TO THE INVENTION

Electrosurgical instruments are instruments that are used to deliver microwave frequency electromagnetic energy to biological tissue, for purposes such as cutting, coagulating or ablating the tissue.

Coagulation of biological tissue is useful during surgery primarily to stop bleeding from the tissue (haemostasis), for example after the tissue has been cut during surgery. Ablation of tissue is useful during surgery to remove/destroy tissue, for example tumours or lesions.

Electrosurgical instruments that can be used to deliver microwave frequency energy into biological tissue for these purposes are known and have been used in surgical procedures in the past. However, the present inventors have realised that existing electrosurgical instruments that can deliver microwave frequency energy into tissue cannot be easily used to provide controlled delivery of microwave energy into tissue in a localised area, which would be useful in many surgical situations, for example when coagulating vessels or ablating small tumours or lesions in the gastrointestinal (GI) tract.

SUMMARY OF THE INVENTION

The inventors have realised that there is a need for an electrosurgical instrument that can be used to provide controlled delivery of microwave frequency energy into tissue in contact with the instrument in a localised manner, for example for the purposes of coagulating the tissue or ablating a small area of the tissue, for example in the gastrointestinal (GI) tract.

The inventors have realised that an advantageous way to achieve controlled delivery of microwave frequency energy into a localised area of tissue would be to couple microwave frequency electromagnetic energy directly to the tissue from an exposed end of a coaxial transmission line (e.g. a coaxial cable) by pressing the exposed end of the coaxial transmission line against the tissue. The inventors have realised that energy delivered into tissue in this manner would be localised in an area of the tissue that is adjacent the exposed end of the coaxial transmission line and symmetrical around a central axis of the coaxial transmission line. Such localised delivery of microwave frequency energy into the tissue could generate controlled coagulation of the tissue in this localised area, or localised ablation, for example.

However, the inventors have realised that biological tissue in contact with an exposed end of a coaxial transmission line would present a low impedance to the microwave frequency energy relative to the impedance of the coaxial transmission line (for example ⅙ of the impedance of the coaxial transmission line), and that there would therefore be a significant impedance mismatch between the coaxial transmission line and the biological tissue. Such an impedance mismatch would lead to reflection of a significant proportion of the microwave frequency energy at the interface between the coaxial transmission line and the tissue, which would limit the efficiency of the instrument and may prevent sufficient microwave energy from being delivered to the tissue.

The inventors have realised that this impedance mismatch problem can be overcome by providing an impedance transformer at the distal end of the coaxial transmission line in order to better match the impedance of the coaxial transmission line to the impedance of the tissue being coagulated, so that the microwave frequency energy is effectively coupled/delivered to the tissue without significant reflection of the energy.

The inventors have realised this can be achieved in practice, while still achieving the advantages of coupling the energy directly to the tissue from an exposed end of a coaxial transmission line, by providing the impedance transformer in the form of a further coaxial transmission line connected to the distal end of the first coaxial transmission line, wherein the further coaxial transmission line has a length and characteristic impedance that are configured to better match the impedance of the first coaxial transmission line to the impedance of the tissue to be coagulated at a desired operating frequency of the instrument.

The inventors have realised that with this configuration the energy can be coupled/delivered directly to a localised area of tissue in contact with the electrosurgical instrument to achieve controllable localised delivery of microwave frequency energy to the tissue, and that the amount of energy that is delivered to the tissue can be increased by the better impedance matching, provided by the further coaxial transmission line.

Therefore, at its most general the present invention relates to an electrosurgical instrument for delivering microwave frequency electromagnetic energy having a predetermined operating frequency into tissue in contact with the instrument, wherein the instrument comprises a first coaxial transmission line having a second coaxial transmission line connected to the distal end thereof, the second coaxial transmission line having a length and a characteristic impedance that are configured to better match the impedance of the first coaxial transmission line to the load impedance at the distal end of the distal coaxial transmission line when the instrument is in contact with the tissue, at the operating frequency.

According to a first aspect of the present invention there is provided an electrosurgical instrument configured for delivering microwave frequency energy having a predetermined operating frequency into tissue having a predetermined characteristic impedance in contact with a distal end of the instrument, the instrument comprising: a proximal coaxial transmission line for conveying microwave frequency energy comprising a first inner conductor, a first outer conductor formed coaxially with the first inner conductor, and a first dielectric layer separating the first inner conductor and the first outer conductor; a distal coaxial transmission line for conveying microwave frequency energy comprising a second inner conductor connected to the first inner conductor, a second outer conductor formed coaxially with the second inner conductor and connected to the first outer conductor, and a second dielectric layer separating the second inner conductor and the second outer conductor; wherein a ratio of an inner diameter of the second outer conductor to the outer diameter of the second inner conductor is such that a characteristic impedance of the distal coaxial transmission line is intermediate between a characteristic impedance of the proximal coaxial transmission line and a load impedance at the distal end of the distal coaxial transmission line when the distal end of the instrument is in contact with the tissue; and wherein a length of the distal coaxial transmission line is such that the distal coaxial transmission line is an impedance transformer that improves the impedance match between the proximal coaxial transmission line and the load impedance at the distal end of the distal coaxial transmission line when the distal end of instrument is in contact with the tissue, at the predetermined operating frequency.

In the instrument according to the first aspect of the present invention, the distal coaxial transmission line acts as an impedance transformer that better matches the impedance of the proximal coaxial transmission line to the load impedance at the distal end of the distal coaxial transmission line when the distal end of instrument is in contact with the tissue, at the predetermined operating frequency. The instrument can therefore be used to more efficiently couple electromagnetic energy into the tissue, because reflection of energy away from the tissue is reduced.

The term load impedance at the distal end of the distal coaxial transmission line means an impedance seen from the distal end of the distal coaxial transmission line (when looking towards the tissue).

The electrosurgical instrument may be used to couple microwave frequency energy into tissue by directly contacting the tissue with the distal end of the distal coaxial transmission line and providing microwave frequency electromagnetic energy to the proximal end of the proximal coaxial transmission line at the predetermined frequency. In this case, the load impedance at the distal end of the distal coaxial transmission line when the distal end of the coaxial transmission line is in contact with the tissue will be determined by the predetermined characteristic impedance of the tissue. However, the load impedance will not be the impedance of a plane wave in the tissue in isolation, but will instead be the impedance of a wave in the tissue with the distal tip of the distal coaxial transmission line present and contacting the tissue. These impedances are different. The exact load impedance to be matched can be determined by simulation, calculation or experimentation, based on the predetermined characteristic impedance of the tissue and on the properties of the distal coaxial transmission line.

Alternatively, as discussed below, a further distal coaxial transmission line may be provided in some embodiments, in which case the electrosurgical instrument may be used to couple microwave frequency energy into the tissue by directly contacting the tissue with the distal end of the further distal coaxial transmission line and providing microwave frequency electromagnetic energy to the proximal end of the proximal coaxial transmission line at the predetermined frequency. In this case, the load impedance at the distal end of the distal coaxial transmission line when the distal end of the further distal coaxial transmission line is in contact with the tissue will depend on both the predetermined characteristic impedance of the tissue and on the properties of the further distal coaxial transmission line, for example the impedance of the further distal coaxial transmission line.

In either case, energy is more efficiently coupled/delivered into the tissue in a localised area of the tissue adjacent to the point of contact with the tissue, such that controlled delivery of microwave frequency energy into the tissue can be achieved in this localised area.

The instrument is optimised for delivering microwave frequency energy having a particular operating frequency to a particular type of tissue having a particular characteristic impedance. Of course, in practice the instrument may be used with an acceptable level of performance with different types of tissues having similar characteristic impedances to the particular characteristic impedance, and/or with microwave frequency energy having a similar frequency to the particular operating frequency.

The phrase "improve the impedance match" means reducing an impedance mismatch between the characteristic impedance of the first coaxial transmission line and the load impedance at the distal end of the distal coaxial transmission line when the distal end of instrument is in contact with the tissue. The phrase "improve the impedance match" may mean reducing a return loss of the instrument due to the impedance mismatch, i.e. reducing a ratio or percentage of the microwave frequency radiation that is reflected away from the tissue (back towards the generator) due to the impedance mismatch.

The phrase "improve the impedance match" may mean reducing an impedance mismatch between a real part (component) of the characteristic impedance of the first coaxial transmission line and a real part (component) of the load impedance at the distal end of the distal coaxial transmission line when the distal end of instrument is in contact with the tissue.

In other words, when referring to impedance matching by the distal coaxial transmission line the impedances being matched may be the real parts (components) of the impedances in question. Thus, a real part of the characteristic impedance of the distal coaxial transmission line may be intermediate between a real part of the characteristic impedance of the proximal coaxial transmission line and a real part of the load impedance at the distal end of the distal coaxial transmission line when the distal end of instrument is in contact with the tissue. Furthermore, the distal coaxial transmission line may be an impedance transformer that improves the impedance match between the real part of the characteristic impedance of the proximal coaxial transmission line and the real part of the load impedance at the distal end of the distal coaxial transmission line when the distal end of instrument is in contact with the tissue.

The term proximal end is used throughout this specification to mean an end that is closest to the end of the instrument into which the microwave frequency electromagnetic energy is input from a generator. The term distal end is used throughout this specification to mean an end that is furthest from the end of the instrument into which the microwave frequency energy is input from a generator, in other words an end closest to the end of the instrument at which the microwave frequency energy is delivered to the tissue.

In practice the tissue is likely to have a lower impedance than the proximal coaxial transmission line. Therefore, in practice the impedance of the distal coaxial transmission line is likely to be less than the impedance of the proximal coaxial transmission line but more than the impedance of the tissue. For example, the impedance of the distal coaxial transmission line may be between 8 Ohms and 30 Ohms, which may be appropriate for a range of different tissue types, or between 8 Ohms and 15 Ohms. The tissue may also have a reactive (imaginary) part (element) of its impedance, as discussed in more detail below. In one embodiment, the impedance of the distal coaxial transmission line may be approximately 10 Ohms. An impedance of the distal coaxial transmission line in the range of 8 Ohms to 15 Ohms would be suitable for many tissue types of interest, and an impedance of up to 30 Ohms would be suitable for fat.

The electrosurgical instrument according to the first aspect of the present invention may have any one, or, to the extent they are compatible, any combination of the following optional features.

The first inner conductor and/or the second inner conductor may be solid. In other words, they are not hollow. They may be solid cylinders, for example a solid wire.

A proximal end of the distal coaxial transmission line may be directly connected to a distal end of the proximal transmission line.

The distal coaxial transmission line may be symmetrical around a central axis thereof. Thus, the resulting power absorption pattern in tissue in contact with a distal end of the distal coaxial transmission line during operation of the instrument may also be symmetrical around the central axis of the distal coaxial transmission line.

The proximal coaxial transmission line may be symmetrical around a central axis thereof.

The proximal and distal coaxial transmission lines may be arranged with central axes thereof aligned on the same line.

The first and/or second inner conductor(s) may be cylindrical. The first and/or second inner conductors may comprise a single metal, or may comprise more than one metal, for example a steel wire plated with copper and/or silver.

The first and/or second outer conductor(s) may be tubular. The first and/or second outer conductors may be formed from a wire braid. The wire braid may be formed from copper wire plated with tin.

A length of the distal coaxial transmission line may be substantially equal to $(2n+1)\lambda/4$, where $\lambda$ is the wavelength in the distal coaxial transmission line of microwave frequency energy having the predetermined operating frequency and n is an integer greater than or equal to 0.

Thus, the distal coaxial transmission line may act as a quarter wave impedance transformer that better matches the impedance of the proximal coaxial transmission line to the load impedance at the distal end of the distal coaxial transmission line when the distal end of instrument is in contact with the tissue.

Where the length of the distal coaxial transmission line is substantially equal to $(2n+1)\lambda/4$, a preferable length of the distal coaxial transmission line is $\lambda/4$, because longer lengths will increase the power losses. However, acceptable performance can be achieved with longer lengths. Essentially, a balance can be struck between achieving a practical (useful) length of the distal coaxial transmission line and achieving an acceptable loss of power in the distal coaxial transmission line.

A length of the distal coaxial transmission line of $(2n+1)\lambda/4$ may provide optimal impedance matching between the proximal coaxial transmission line and the load impedance at the distal end of the distal coaxial transmission line when the distal end of instrument is in contact with the tissue at the predetermined operating frequency. However, acceptable (non-optimal) impedance matching performance may be achieved with a length that is not exactly equal to $(2n+1)\lambda/4$, for example a length that is up to 10% greater than or less than $(2n+1)\lambda/4$, or a length that is up to 20% greater than or less than $(2n+1)\lambda/4$. With larger or smaller lengths the proportion of microwave frequency energy that is reflected and therefore not delivered into the tissue will be greater, so the efficiency of the electrosurgical instrument will be less. However, an acceptable (sub-optimal) efficiency may still be achieved.

Furthermore, other aspects of the geometry of the distal coaxial transmission line or the tissue load may have an effect on the optimal length of the distal coaxial transmission line for impedance matching. For example, end effects such as an abrupt end of the distal coaxial transmission line, the properties of the tissue load, and step changes in the diameters of the inner and outer conductors of the distal coaxial transmission line may have an equivalent effect to lumped components such as inductors or capacitors, and may therefore introduce small phase changes that have a similar effect to a shortening or lengthening of the transmission line. These effects may be effectively cancelled out in practice by making small changes in the length of the distal coaxial transmission line relative to a length of $(2n+1)\lambda/4$. Thus, in practice the optimal length of the distal coaxial transmission for impedance matching may not be exactly equal to $(2n+1)\lambda/4$. The optimal length for the distal coaxial transmission line for a particular configuration may be determined by calculation, by simulation, or by experimentation.

As mentioned above, the relevant $\lambda$ for determining the optimal length of the distal coaxial transmission line is the wavelength of the microwave frequency radiation in the distal coaxial transmission line. The necessary length of the second coaxial transmission line for the length to be equal to $(2n+1)\lambda/4$ depends at least in part on the geometry of the distal coaxial transmission line. For example, if the distal coaxial transmission line has a conical shape (as in one of the example embodiments described below), the wavelength changes with distance from the tip of the conical shape. This variation can be described mathematically using Bessel functions. Close to the tip of the conical shape the wavelength is significantly longer than it is several wavelengths from the tip. If this variation is not taken into account, the number of wavelengths calculated between two points of the conical shape may be out by a significant fraction of a wavelength. With such a conical shape the length of the distal coaxial transmission line that is equal to a length of $(2n+1)\lambda/4$ is greater than the equivalent length for a uniform cylindrical shape of the distal coaxial transmission line.

The electrosurgical instrument may be for coagulating tissue. The term coagulating tissue may mean coagulating blood within the tissue, for example coagulating blood within a vessel or lumen within the tissue. Coagulation of the tissue is achieved through heating of the tissue by the delivery of microwave energy into the tissue.

Alternatively, the electrosurgical instrument may be for another purpose, for example the electrosurgical instrument may be for ablating tissue. Thus, the electrosurgical instrument may be configured for delivering microwave frequency energy into a localised area of tissue in contact with the distal end of the distal coaxial transmission line in order to ablate the tissue (destroy or remove the tissue) by heating it. This may be useful, for example, when removing small tumours or lesions of the surface of biological tissue.

The ratio of the inner diameter of the second outer conductor to the outer diameter of the second inner conductor may be such that a characteristic impedance of the distal coaxial transmission line is substantially equal to $\sqrt{Z_{in}Z_L}$, where $Z_{in}$ is the characteristic impedance of the proximal coaxial transmission line and $Z_L$ is load impedance at the distal end of the distal coaxial transmission line when the distal end of instrument is in contact with the tissue. For example, where the distal end of the distal coaxial transmission line is used to contact the tissue directly, $Z_L$ is based on the predetermined characteristic impedance of the tissue (specifically, it is the impedance of a wave in the tissue with the distal tip of the distal coaxial transmission line present and contacting the tissue).

When the characteristic impedance of the distal coaxial transmission line is equal to $\sqrt{Z_{in}Z_L}$, the impedance of the proximal coaxial transmission line may be exactly matched to the load impedance at the distal end of the distal coaxial transmission line when the distal end of instrument is in contact with the tissue (assuming an optimal length of the distal coaxial transmission line) and the maximum amount of microwave frequency energy may be delivered to the tissue. This value of the ratio is therefore a particularly advantageous value. Of course, acceptable performance of the instrument may be achievable with impedances of the distal coaxial transmission line that differ from this value. For example, acceptable (non-optimal) performance of the electrosurgical instrument may be achieved with an impedance of the distal coaxial transmission line that is up to 10% higher or lower than the optimal value, or up to 20% higher or lower than the optimal value.

The second inner conductor, second outer conductor and second dielectric layer may be exposed at a distal end face of the distal coaxial transmission line for contacting the tissue. Thus, microwave energy may be coupled/delivered to the tissue by contacting the tissue with the exposed end face of the distal coaxial transmission line. As mentioned above, in this case the load impedance at the distal end of the distal coaxial transmission line when the distal end of instrument is in contact with the tissue is based on the predetermined characteristic impedance of the tissue (specifically the load impedance is the impedance of a wave in the tissue with the distal tip of the distal coaxial transmission line present and contacting the tissue).

The exposed end face of the distal coaxial transmission line may be substantially perpendicular to a central axis of the distal coaxial transmission line.

The exposed end face of the distal coaxial transmission line may be substantially flat.

The electrosurgical instrument may comprise a further distal coaxial transmission line comprising a third inner conductor connected to the second inner conductor, a third outer conductor formed coaxially with the third inner conductor and connected to the second outer conductor, and a third dielectric layer separating the third inner conductor and the third outer conductor.

The third inner conductor, third outer conductor and third dielectric later may be exposed at a distal end face of the further distal coaxial transmission line for contacting the tissue. Thus, microwave frequency energy may be coupled/delivered to the tissue by contacting the tissue with the exposed end face of the distal coaxial transmission line. As mentioned above, in this case the load impedance at the distal end of the distal coaxial transmission line when the distal end of further distal coaxial transmission line is in contact with the tissue depends on both the predetermined characteristic impedance of the tissue and on the properties of the further distal coaxial transmission line, including the impedance of the further distal coaxial transmission line.

The further distal coaxial transmission line may be a length of coaxial cable. The further distal coaxial transmission line may comprise the same type of coaxial cable as the proximal coaxial transmission line.

The cross-section of the further distal coaxial transmission line may be the same as the cross-section of the proximal coaxial transmission line. For example, the diameters of the first and third inner conductors may be the same and the diameters of the first and third outer conductors may be the same.

The further distal coaxial transmission line may be made from the same materials as the proximal coaxial transmission line.

A characteristic impedance of the further distal coaxial transmission line may be the same as a characteristic impedance of the proximal coaxial transmission line. For example, the proximal coaxial transmission line and the further distal coaxial transmission line may both have an impedance of 50 Ohms.

A length of the further distal coaxial transmission line may be such that the further distal coaxial transmission line substantially cancels out a reactive part of the predetermined characteristic impedance of the tissue at the predetermined operating frequency. Thus, the further distal coaxial transmission line cancels out the reactive part of the predetermined characteristic impedance and the distal coaxial transmission line then matches (or improves the match between) the subsequent purely real impedance and the real part of the characteristic impedance of the proximal coaxial transmission line. Thus, both the real and reactive parts of the impedances are accounted for by the combination of the distal coaxial transmission line and the further distal coaxial transmission line.

As mentioned above, the subsequent purely real impedance that is matched to the real part of the characteristic impedance of the proximal coaxial transmission depends on both the predetermined characteristic impedance of the tissue and on the properties of the further distal coaxial transmission line, including the impedance of the further distal coaxial transmission line.

An appropriate length of the further distal coaxial transmission line can be determined by calculation based on the parameters of the desired implementation, for example the properties of the tissue load and the properties of the microwave radiation. The appropriate length can also be determined by computer simulation/modelling or experimentation.

The further distal coaxial transmission line may be rigid. In other words, the further distal coaxial transmission line may be non-flexible. This may help during the operation of the electrosurgical instrument, because the further distal coaxial transmission line forms a rigid instrument tip that can be pressed against tissue without the instrument tip deforming under the pressure.

The electrosurgical instrument may comprise an open-circuited or short-circuited stub connected in parallel to the further distal coaxial transmission line. The stub may be connected to the distal end of the distal coaxial transmission line. The properties of the stub (e.g. its length and characteristic impedance) may be chosen to cancel out the reactive part of the predetermined characteristic impedance of the tissue. In terms of a Smith Chart, the further distal coaxial transmission line may be considered to move the reactive part of the impedance onto the constant conductance circle and the open-circuited or short-circuited stub connected to the distal coaxial transmission line nulls or cancels out the reactive impedance (+/−jB) seen at the proximal end of the distal coaxial transmission line.

A characteristic impedance of the stub may be the same as a characteristic impedance of the further distal coaxial transmission line. Alternatively, a characteristic impedance of the stub may not be the same as a characteristic impedance of the further distal coaxial transmission line.

The electrosurgical instrument may comprise a plurality of the open-circuited or short-circuited stubs connected in parallel to the further distal coaxial transmission line.

The distal coaxial transmission line may be rigid. In other words, the distal coaxial transmission line may be non-flexible. This may help during the operation of the electrosurgical instrument, because the distal coaxial transmission line forms a rigid instrument tip that can be pressed against tissue to be coagulated without the instrument tip deforming under the pressure.

The predetermined operating frequency may be 5.8 GHz. In other words, the length of the distal coaxial transmission line may be such that the distal coaxial transmission line is an impedance transformer that improves the impedance match between the proximal coaxial transmission line and the load impedance at the distal end of the distal coaxial transmission line when the distal end of instrument is in contact with the tissue at a predetermined operating frequency of 5.8 GHz. For example, the length of the distal coaxial transmission line may be substantially equal to $(2n+1)\lambda/4$, where $\lambda$ is the wavelength in the distal coaxial transmission line of microwave frequency energy having a predetermined operating frequency of 5.8 GHz.

5.8 GHz is a suitable frequency for achieving controllable delivery of microwave frequency energy into tissue in a localised area, for example to achieve coagulation of the tissue.

A separation between the outer diameter of the second inner conductor and the inner diameter of the second outer conductor may be less than a separation between an outer diameter of the first inner conductor and an inner diameter of the first outer conductor. In other words, a thickness of the second dielectric layer may be less than a thickness of the first dielectric layer. An advantage of reducing the separation between the inner and outer conductors in the distal coaxial transmission line is that the characteristic impedance of the distal coaxial transmission line is made lower.

However, in alternative embodiments the separation between the outer diameter of the second inner conductor and the inner diameter of the second outer diameter may instead be greater than the separation between the outer diameter of the first inner conductor and the inner diameter of the first outer conductor, particularly if a high dielectric constant material such a titanium dioxide is used in the second dielectric layer.

The outer diameter of the second inner conductor may be greater than the outer diameter of the first inner conductor. In other words, the second inner conductor may be wider than the first inner conductor. Alternatively, the outer diameter of the second inner conductor may be less than the outer diameter of the first inner conductor. In other words, the second inner conductor may be narrower than the first inner conductor.

The outer diameter of the second outer conductor may be greater than the outer diameter of the first outer conductor.

In other words, the second outer conductor may be wider than the first outer conductor. Alternatively, the outer diameter of the second outer conductor may be less than the outer diameter of the first outer conductor. In other words, the second outer conductor may be narrower than the first outer conductor.

Where there is a difference in diameter between the first inner conductor and the second inner conductor, or between the first outer conductor and the second outer conductor, a small adjustment may be made to the length of the distal coaxial transmission line to compensate for the effect of the step or steps in diameter. The appropriate size of the adjustment may be calculated, looked up, or determined experimentally or by simulation.

Where there is a difference in diameter between the first inner conductor and the second inner conductor, and between the first outer conductor and the second outer conductor, an axial position of the step in diameter between the inner conductors may be different to an axial position of the step in diameter between the outer conductors, in order to compensate for the effects of the steps in diameter.

The distal coaxial transmission line may have a greater external diameter than the proximal coaxial transmission line. In other words, the distal coaxial transmission line may be wider than the proximal coaxial transmission line.

The second dielectric layer may be made from a different dielectric to the first dielectric layer. The second dielectric layer may have a higher relative permittivity than the first dielectric layer. For example, the second dielectric layer may be made from a glass ceramic dielectric such as MACOR. The first dielectric material may be PTFE. Using a dielectric with a higher relative permittivity in the second dielectric layer results in a lower impedance of the second dielectric layer for the same thickness of the second dielectric layer.

The characteristic impedance of the proximal coaxial transmission line may be 50 Ohms.

The proximal coaxial transmission line may be a coaxial cable. For example, the coaxial cable may be Sucoform 86 coaxial cable, or Sucoform 47 coaxial cable.

The distal coaxial transmission line may be a coaxial cable.

The distal coaxial transmission may line be tapered from a wider proximal end thereof to a narrower distal end thereof. In other words, the distal coaxial transmission line may narrow linearly from the proximal end thereof to the distal end thereof, so that the distal end is narrower than the proximal end. This may result in the distal coaxial transmission line having a truncated cone shape. The distal end of the distal coaxial transmission line may have a diameter half the diameter of the proximal end. This configuration of the distal coaxial transmission line results in the microwave energy being delivered into a smaller area of the tissue at the distal end of the distal coaxial transmission line. This further localisation of the delivery of microwave frequency energy into the tissue may be particularly useful in some surgical procedures, for example when trying to coagulate a small vessel, or when trying to ablate a small surface tumour or lesion.

In an alternative embodiment the distal coaxial transmission line may instead be tapered from a wider distal end thereof to a narrower proximal end thereof. In other words the tapering of the distal coaxial transmission line may be in the opposite direction to that described immediately above.

Of course, other shapes for the distal coaxial transmission line are also possible.

Where the distal coaxial transmission line is tapered, the ratio of the inner diameter of the second outer conductor to the outer diameter of the second inner conductor may be substantially constant along the distal coaxial transmission line, so that its impedance is substantially uniform along its length.

The instrument may be configured for delivering microwave frequency energy having the predetermined operating frequency into tissue having a predetermined characteristic impedance in the range of 45 to 180 Ohms, or in the range 45 to 60 Ohms. For example, many tissues of interest may have impedances of between approximately 45 and 60 Ohms. Nail may have an impedance of approximately 120 Ohms, and fat and bone may have impedances of approximately 180 Ohms. As mentioned above, the tissue may also have a reactive (imaginary) component to its impedance.

The electrosurgical instrument may comprise a plurality of the distal coaxial transmission lines for improving the impedance match between the proximal coaxial transmission line and the tissue at the predetermined operating frequency. In other words, there may be a plurality of the distal coaxial transmission lines connected in series, each of which is configured (in terms of the ratio of the inner and outer diameters and the length) to improve the impedance match between the proximal coaxial transmission line and the tissue at the predetermined operating frequency. This arrangement may be particularly beneficial when the characteristic impedance of the proximal coaxial transmission line differs significantly from the impedance of the tissue, because the impedance matching can be carried out incrementally/gradually over the plurality of distal coaxial transmission lines According to a second aspect of the present invention, there may be provided an electrosurgical system comprising:
an electrosurgical instrument according to the first aspect of the present invention, optionally with one or more of the optional features described above; and
an electrosurgical generator connected to a proximal end of the proximal coaxial transmission line;
wherein the electrosurgical generator is configured to supply the proximal coaxial transmission line with microwave frequency electromagnetic energy having the predetermined operating frequency.

For example, the controller may be pre-set or programmed to supply the proximal coaxial transmission line with microwave frequency energy having the predetermined operating frequency.

The electrosurgical system may be for coagulating tissue, or for ablating tissue.

The electrosurgical system may comprise a controller for controlling the electrosurgical generator; and the controller may be configured to control the power and/or duration of the microwave frequency energy supplied by the generator to limit the amount of microwave frequency energy delivered to the tissue to below a predetermined amount.

For example, the controller may be configured to control the power and/or duration of the microwave frequency energy to keep the amount of microwave frequency energy delivered to the tissue below an amount at which perforation of the tissue, or some other unwanted effect, is known to start to occur, or below an amount a safe margin below this amount. Thus, the controller may operate to prevent the generator from supplying more energy than this, for example by stopping the generator from supplying microwave energy when the limit is reached.

The amount of microwave frequency energy at which perforation, or some other unwanted effect of the microwave frequency energy, starts to occur may be known in advance, e.g. from calculation or experiment. The controller may therefore be programmed in advance with relevant information for the type of tissue which is to be treated using the instrument and for the type of treatment required, e.g. coagulation or ablation. For example, the controller may be programmed in advance with a particular value for the upper limit of microwave energy that can be supplied to the tissue. Alternatively, the controller may be programmed with particular combinations of power and duration that can be supplied by the generator for that tissue.

Thus, it may be possible to use the instrument with confidence that perforation of the tissue or some other unwanted effect will not occur, which is an important consideration in a clinical setting.

The electrosurgical system may comprise a sensor for sensing information indicative of the amount of microwave frequency energy delivered to the tissue. For example, the sensor may sense an amplitude of the microwave frequency energy being transmitted towards the tissue and an amplitude of microwave frequency energy being reflected back from the tissue and may use this information to determine the amount of energy being delivered to the tissue. Of course, this functionality may be performed by a plurality of sensors instead of by a single sensor.

The controller may be configured to control the generator to provide a power of 15 W for a period of up to four seconds. The present inventors have realised that this results in enough energy being delivered to the tissue to achieve coagulation of the tissue while safely avoiding perforation of the tissue or other unwanted effects.

According to a third aspect of the present invention there may be provided a method of manufacturing an electrosurgical instrument according to the first aspect of the present invention, optionally with any one or more of the optional features described above, the method comprising:
determining a ratio of the inner diameter of the second outer conductor to the outer diameter of the second inner conductor that results in the characteristic impedance of the distal coaxial transmission line being intermediate between a characteristic impedance of the proximal coaxial transmission line and the load impedance at the distal end of the distal coaxial transmission line when the distal end of instrument is in contact with the tissue;
setting the ratio of the inner diameter of the second outer conductor to the outer diameter of the second inner conductor to be the determined ratio;
determining a length of the distal coaxial transmission line that results in the distal coaxial transmission line being an impedance transformer that improves the impedance match between the proximal coaxial transmission line and the load impedance at the distal end of the distal coaxial transmission line when the distal end of instrument is in contact with the tissue; and
setting the length of the distal coaxial transmission line to be the determined length.

The method according to the third aspect of the present invention can be used to manufacture an electrosurgical instrument that is optimised to be used for coagulating a particular type of tissue at a particular operating frequency.

According to the method, the ratio of the diameters of the inner and outer conductors of the distal coaxial transmission line and the length of the distal coaxial transmission line that are necessary for better impedance matching to the specified load impedance at the distal end of the distal coaxial transmission line when the distal end of instrument is in contact with the tissue at the specified operating frequency are determined. An electrosurgical instrument having the calculated properties of the distal coaxial transmission line is then manufactured. The resulting electrosurgical instrument is optimised for use in coagulating the specified tissue having the specified characteristic impedance at the specified operating frequency.

The method according to the third aspect of the present invention may have any one, or, to the extent they are compatible, more than one of the following optional features.

The method may comprise: determining the wavelength $\lambda$ in the distal coaxial transmission line of microwave frequency energy having the predetermined operating frequency; and setting the length of the distal coaxial transmission line to be substantially equal to $(2n+1)\lambda/4$, where n is an integer greater than or equal to 0, based on the determined wavelength $\lambda$. As discussed above, this may be (approximately) an optimal length of the distal coaxial transmission line in terms of achieving optimal impedance matching between the proximal coaxial transmission line and the tissue.

The method may comprise determining a ratio of the inner diameter of the second outer conductor to the outer diameter of the second inner conductor that results in the characteristic impedance of the distal coaxial transmission line being substantially equal to $\sqrt{Z_{in}Z_L}$, where $Z_{in}$ is the characteristic impedance of the proximal coaxial transmission line and $Z_L$ is the load impedance at the distal end of the distal coaxial transmission line when the distal end of instrument is in contact with the tissue, and setting the ratio of the inner diameter of the second outer conductor to the outer diameter of the second inner conductor to be the determined ratio. As discussed above, this impedance of the distal coaxial transmission line may provide optimum impedance matching.

Determining the wavelength and/or determining the ratio may comprise calculating the wavelength and/or the ratio. Alternatively, determining the wavelength and/or determining the ratio may comprise finding/looking-up the relevant information in a table, database or other program or document.

The method may comprise calculating $\sqrt{Z_{in}Z_L}$, and calculating the ratio of the inner diameter of the second outer conductor to the outer diameter of the second inner conductor that results in a characteristic impedance of the distal coaxial transmission line equal to $\sqrt{Z_{in}Z_L}$. The characteristic impedance of the proximal coaxial transmission line may be calculated, measured, or looked up in a table, database or data sheet, for example. The characteristic impedance of the target tissue may similarly be calculated, measured, or looked up in a table, database or data sheet, for example.

The method may comprise calculating the wavelength in the distal coaxial transmission line of microwave frequency energy having the predetermined operating frequency based on the relative permittivity of the second dielectric layer. Thus, the wavelength may be calculated based on knowledge of the relative permittivity of the dielectric material in the second dielectric layer and known physical constants.

Where the electrosurgical instrument comprises the further distal coaxial transmission line, the method may comprise: determining a length of the further distal coaxial transmission line that results in the reactive part of the predetermined characteristic impedance of the tissue being cancelled out; and setting the length of the further distal coaxial transmission line to be substantially equal to the determined length.

Any of the first, second or third dielectric materials in any of the aspects mentioned above may be a gas, such as air, or a solid or liquid.

BRIEF DESCRIPTION OF THE DRAWINGS

Embodiments of the present invention will now be discussed, by way of example only, with reference to the accompanying Figures, in which.

DETAILED DESCRIPTION; FURTHER OPTIONS AND PREFERENCES

As discussed above, the inventors have realised that an advantageous way to achieve controlled delivery of microwave frequency radiation into tissue in a localised area would be to couple microwave frequency energy directly to the tissue from an exposed end of a coaxial transmission line (e.g. a coaxial cable) by pressing the exposed end of the coaxial transmission line against the tissue.

However, the inventors have realised that biological tissue in contact with an exposed end of a coaxial transmission line would present a low impedance to the microwave frequency energy relative to the impedance of the coaxial transmission line, and that there would therefore be a significant impedance mismatch between the coaxial transmission line and the biological tissue.

The inventors have realised that this problem can be overcome by providing an impedance transformer at the distal end of the coaxial transmission line in order to better match the impedance of the coaxial transmission line to the impedance of the tissue, so that the microwave frequency energy is more effectively coupled/delivered to the tissue with less significant reflection of the energy.

The present inventors have realised this can be achieved in practice, while still achieving the advantages of coupling the energy directly to the tissue from an exposed end of a coaxial transmission line, by providing the impedance transformer in the form of a further coaxial transmission line connected to the distal end of the first coaxial transmission line, wherein the further coaxial transmission line has a length and characteristic impedance that are configured to better match the impedance of the first coaxial transmission line to the load impedance at the distal end of the further coaxial transmission line.

Figure 1:
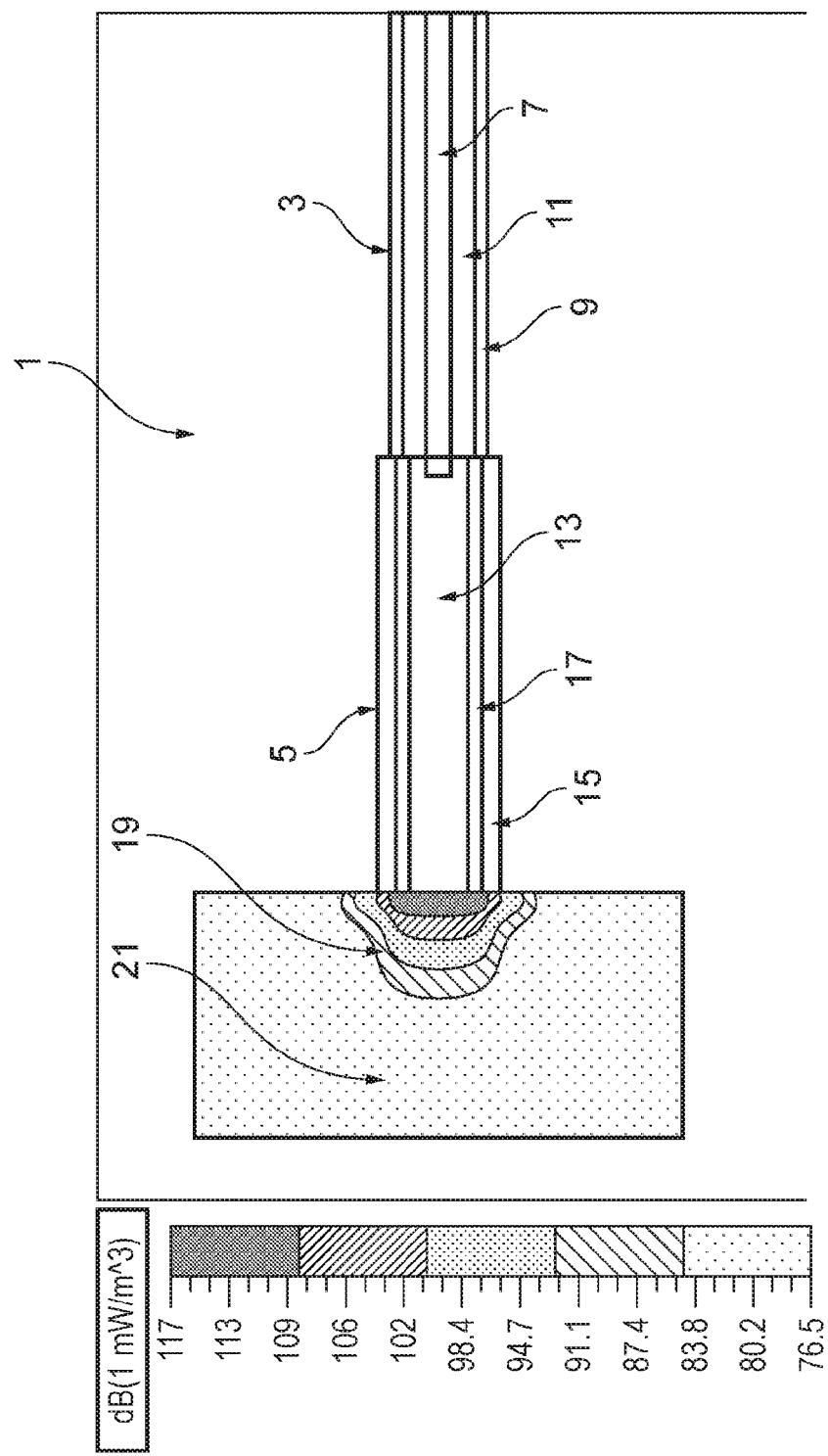
FIG. 1 shows a computer simulation of an electrosurgical instrument according to an embodiment of the present invention being used to coagulate liver tissue.

Therefore, in a first embodiment of the present invention illustrated in FIG. 1, there is provided an electrosurgical instrument 1 comprising a first (proximal) coaxial transmission line 3 for conveying microwave frequency energy from a proximal (rear) end thereof to a distal (front) end thereof. Furthermore, there is provided a second (distal) coaxial transmission line 5 for conveying microwave frequency energy from a proximal (rear) end thereof to a distal (front) end thereof. The second coaxial transmission line 5 is connected at the proximal end thereof to the distal end of the first coaxial transmission line 3, so that microwave frequency energy can be conveyed directly from the first coaxial transmission line 3 to the second coaxial transmission line 5.

The first and second coaxial transmission lines 3, 5 are both symmetrical around respective central axes thereof. Furthermore, the first and second coaxial transmission lines 3, 5 are aligned with each other end to end so that their central axes lie on the same line.

The first coaxial transmission line 3 comprises a cylindrical first inner conductor 7, a tubular first outer conductor 9 and a tubular first dielectric layer 11 separating the first inner conductor 7 and the first outer conductor 9. The first dielectric layer 11 is provided directly on an external surface of the first inner conductor 7, and the first outer conductor 9 is provided directly on an external surface of the first dielectric layer 11.

In this embodiment the first coaxial transmission line is 50 Ohm Sucoform 86 coaxial cable. The first inner conductor 7 has a diameter of 0.53 mm, the first outer conductor 9 has an inner diameter of 1.65 mm (and therefore the first dielectric layer 11 has an outer diameter of 1.65 mm), and the first outer conductor 9 has an outer diameter of 2.1 mm. Of course, in other embodiments a different type of coaxial cable with different dimensions and properties, or a different type of coaxial transmission line, may be used instead.

In this embodiment the first dielectric layer 11 is made from PTFE having a relative permittivity of 2.1. Of course, in other embodiments a different dielectric material may be used.

In this embodiment the first inner conductor 7 is a metal wire. Specifically, the first inner conductor 7 is a steel wire plated with copper and silver. The first outer conductor 9 is a metal braid. Specifically, the first outer conductor 9 is a braid formed from copper wire plated with tin. Of course, in other embodiments different materials may be used for the first inner and outer conductors 7, 9.

The length of the first coaxial transmission line 3 is not critical to the operation of the instrument 1 described below and can be chosen based on the particular environment in which the instrument 1 is intended to be used.

The second coaxial transmission line 5 comprises a cylindrical second inner conductor 13, a tubular second outer conductor 15 and a tubular second dielectric layer 17 separating the second inner conductor 13 and the second outer conductor 15. The second dielectric layer 17 is provided directly on an external surface of the second inner conductor 13, and the second outer conductor 15 is provided directly on an outer surface of the second dielectric layer 17.

In this embodiment the second inner conductor 13 has a diameter of 1.2 mm, meaning the second inner conductor 13 is wider than the first inner conductor 7, and the second outer conductor 15 has an inner diameter of 1.8 mm (and the second dielectric layer 17 therefore has an outer diameter of 1.8 mm). The outer diameter of the second outer conductor 15 is wider than the outer diameter of the first outer conductor 9. Of course, in other embodiments the second inner and outer conductors 13, 15 may have different dimensions. In this embodiment, the outer diameter of the second outer conductor 15 is 2.5 mm.

In this embodiment the second dielectric layer 17 is a glass ceramic dielectric. Specifically, the second dielectric layer 17 is MACOR® and has a relative permittivity of 5.67 (which value may be frequency dependent, and thus depend on the specific frequency of microwave radiation with which the electrosurgical instrument is being used). Of course, in other embodiments a different dielectric material may be used instead.

The second inner conductor 13 may comprise a solid cylinder of stainless steel. The outer surface of the second inner conductor 13 may be coated, for example plated, with silver. Of course, other materials may be used for the second inner conductor 13.

The second outer conductor 15 may comprise a hollow tube of stainless steel. The inner surface of the second outer conductor 15 may be coated, for example plated, with silver. Of course, other materials may be used for the second outer conductor 15.

The second inner conductor 13 is connected to the distal end of the first inner conductor 7 with their central axes aligned. The second outer conductor 15 is also connected to the distal end of the first outer conductor 9 with their central axes aligned. Thus, microwave frequency energy can be conveyed from the first coaxial transmission line 3 to the second coaxial transmission line 5. The first and second coaxial transmission lines 3, 5 may therefore have overlapping central axes.

In this embodiment the second dielectric layer is thinner than the first dielectric layer.

The second inner conductor 13, second outer conductor 13 and second dielectric layer 17 are exposed at a planer distal end face of the second coaxial transmission line 5. The planar distal end face of the second coaxial transmission line 5 can be pressed against tissue in order to deliver microwave frequency energy into the tissue, as described further below.

The electrosurgical instrument 1 shown in FIG. 1 can be configured to coagulate a particular type of tissue having a particular impedance using microwave energy having a particular frequency. This is achieved by configuring the length of the second coaxial transmission line 5 and the ratio of the inner diameter of the second outer conductor 15 to the diameter of the second inner conductor 13 so that the second coaxial transmission line 5 functions as an impedance transformer that better matches the characteristic impedance of the first coaxial transmission line 3 to the characteristic impedance of the tissue at the particular frequency.

The theory of impedance transformers is well known and understood in the technical field and therefore a detailed description is not repeated here.

Preferably, the second coaxial transmission line 5 is configured to exactly match the impedance of the first coaxial transmission line 3 to the impedance of the tissue, so that the maximum amount of microwave energy is delivered to the tissue. Of course, acceptable performance of the electrosurgical instrument 1 can be achieved without exactly matching the impedances, because a minor impedance mismatch (for example up to 10%, or up to 20%) may lead to reflection of only a minor amount of microwave energy away from the tissue.

There are two requirements for the second coaxial transmission line 5 to function as an impedance transformer that better matches the characteristic impedance of the first coaxial transmission line 3 to the characteristic impedance of the liver tissue at the predetermined operating frequency. Firstly, the length of the second coaxial transmission line 5 must be such that the second coaxial transmission line 5 is an impedance transformer that improves the impedance match between the first coaxial transmission line 3 and the tissue at the predetermined operating frequency. For example, the second coaxial transmission line may have a length that is substantially equal to $(2n+1)\lambda/4$. Secondly, the impedance of the second coaxial transmission line 5 must be intermediate between the impedance of the first coaxial transmission line 3 and the impedance of the tissue being coagulated. For optimal impedance matching, the impedance of the second coaxial transmission line 5 must be substantially equal to $\sqrt{Z_{in}Z_L}$, where $Z_{in}$ is the characteristic impedance of the first coaxial transmission line 3 and $Z_L$ is the predetermined characteristic impedance of the tissue.

In the dielectric material of the second dielectric layer 17 the microwave frequency energy travels as a speed v, where:

$$v = \frac{c}{\sqrt{\mu_r \varepsilon_r'}} \quad (1)$$

where c is the speed of light, $\mu_r$ is the relative permeability of the dielectric material and $\varepsilon_r$ is the relative permittivity (the dielectric constant) of the dielectric material.

Assuming the dielectric material is non-magnetic and therefore has a relative permeability of 1, the microwave frequency energy travels at a speed in the second dielectric layer 17:

$$v = \frac{c}{\sqrt{\varepsilon_r}}. \quad (2)$$

The wavelength $\lambda$ of the microwave frequency energy in the second dielectric layer 17 is therefore given by:

$$\lambda = \frac{c}{f\sqrt{\varepsilon_r'}} \quad (3)$$

where f is the frequency of the microwave frequency energy.

Thus, using equation (3) the wavelength in the second coaxial transmission line 5 of microwave energy having the desired operating frequency can be determined based on the relative permittivity (dielectric constant) of the dielectric material, which can be looked up, calculated of found by experimentation. The length of the second coaxial transmission line 5 that is equal to $(2n+1)\lambda/4$ can then easily be determined, and the length of the second coaxial transmission line 5 in the electrosurgical instrument 1 can be set to be substantially equal to the calculated length.

Alternatively, as discussed above, the optimal length of the second coaxial transmission line 5 may be different to this, because it may also be affected by the specific geometry of the second coaxial transmission line 5. Thus, the optimal length may be calculated based on the geometry of the second coaxial transmission line 5, possibly in addition to using the wavelength in the second coaxial transmission line 5 calculated as described above. Alternatively, the optimal length may be determined based on simulation or experimentation. The optimal length is the length that minimises the return loss, i.e. minimises the amount or proportion of the reflected microwave frequency energy, which corresponds to maximising the impedance match between the first coaxial transmission line 3 and the tissue. Of course, the actual length of the second coaxial transmission line does not have to be the exact optimal length, because other similar lengths may also give acceptable (non-optimal) performance.

The impedance of a coaxial cable is given by equation (4).

$$Z_0 = 60\sqrt{\frac{\mu_r}{\varepsilon_r}} \ln\left(\frac{D}{d}\right) \quad (4)$$

where $\mu_r$ is the relative permeability of the dielectric material, $\varepsilon_r$ is the relative permittivity (the dielectric constant) of the dielectric material, D is the inner diameter of the outer conductor and d is the outer diameter of the inner conductor. Assuming the dielectric material is non-magnetic and therefore has a relative permeability of 1, the impedance of the coaxial transmission line is given by equation (5).

$$Z_0 = \frac{60}{\sqrt{\varepsilon_r}} \ln\left(\frac{D}{d}\right) \quad (5)$$

According to equation (5), the impedance of the coaxial cable is determined solely by the ratio of the inner diameter of the outer conductor to the outer diameter of the inner conductor, for a particular dielectric material with a particular relative permittivity. Thus, using equation (5) the necessary ratio of the inner diameter of the outer conductor to the outer diameter of the inner conductor to provide a coaxial cable having a particular impedance can be calculated.

Thus, equation (5) can be used to calculate the ratio of the inner diameter of the second outer conductor 15 to the outer diameter of the second inner conductor 13 that results in the characteristic impedance of the second coaxial transmission line 5 being intermediate between the characteristic impedance of the first coaxial transmission line 3 and the tissue, and the ratio in the electrosurgical instrument can be set to be the calculated value.

Preferably, a ratio is calculated that results in the characteristic impedance of the second coaxial transmission line 5 being substantially equal to $\sqrt{Z_{in}Z_L}$, where $Z_{in}$ is the characteristic impedance of the first coaxial transmission line and $Z_L$ is the predetermined characteristic impedance of the tissue, because this provides exact impedance matching between the first coaxial transmission line and the tissue and therefore maximises the amount of microwave energy delivered to the tissue.

Appropriate specific diameters of the second inner and outer conductors may be determined based on a number of variables, including the corresponding diameters in the first coaxial transmission line 1, the geometry of the tissue to which the microwave frequency energy is being delivered, and by the frequency of the microwave frequency energy.

In the computer simulation illustrated in FIG. 1, the electrosurgical instrument 1 is configured for coagulating liver tissue using microwave frequency energy having a characteristic frequency of 5.8 GHz. Of course, in other embodiments the desired operating frequency may be different, and/or the desired tissue to be coagulated (and the corresponding characteristic impedance) may be different and/or the instrument may be for achieving an effect other than coagulation, such as ablation.

In this computer simulation the 50 ohm Sucoform 86 cable was modelled as being 10 mm long, for simplicity.

Simulations were carried out using CST Microwave Studio over a bandwidth from 3.3 GHz to 8.3 GHz, with a centre frequency of 5.8 GHz. A liver load was modelled placed directly against the open circuit end of the distal coaxial transmission line. The impedance of the liver load was modelled as being 58+j10.6 Ohms. This corresponds to modelling the liver load as having a dielectric constant of approximately 38 compared to the dielectric constant of 5.67 for the MACOR dielectric in the second coaxial transmission line 5.

Initially a second inner conductor 13 diameter of 1 mm and a second dielectric layer 17 outer diameter of 1.65 mm were selected for the second coaxial transmission line 5, which had an outer diameter of 2.5 mm. Using these parameters it was found by performing various simulations that the ideal length of the second coaxial transmission line 5 for maximising the amount of microwave energy delivered to the liver tissue was close to 9 mm.

With the length of the second coaxial transmission line 5 set at 9 mm the outer diameters of the second inner conductor 13 and the second dielectric layer 17 were varied and it was found that a second inner conductor 13 outer diameter of 1.2 mm and a second dielectric layer 17 outer diameter of 1.8 mm gave a good match to the liver tissue at an operating frequency of 5.8 GHz with a reasonable bandwidth.

The performance of the electrosurgical instrument was checked in the simulations to determine the pattern of absorption in the tissue and the level of radiation in unwanted directions, and the performance was found to be acceptable.

FIG. 1 shows a computer simulation of an electrosurgical instrument 1 according to an embodiment of the present invention being used to coagulate liver tissue in contact with the distal end of the instrument 1. The length and diameter parameters of the second coaxial transmission line 5 were set to the optimal parameters determined above.

It can be seen in FIG. 1 that the power absorption pattern 19 in the liver tissue 21 in the simulation is localised in an area of the liver tissue 21 directly in contact with the distal end of the distal coaxial transmission line 5, and is circularly symmetrical about the shared central axis of the first and second coaxial transmission lines.

This result demonstrates that with the present invention it is possible to achieve controlled localised delivery of power into tissue in contact with the electrosurgical instrument in order to cause controlled localised coagulation in that area of tissue.

Figure 2:
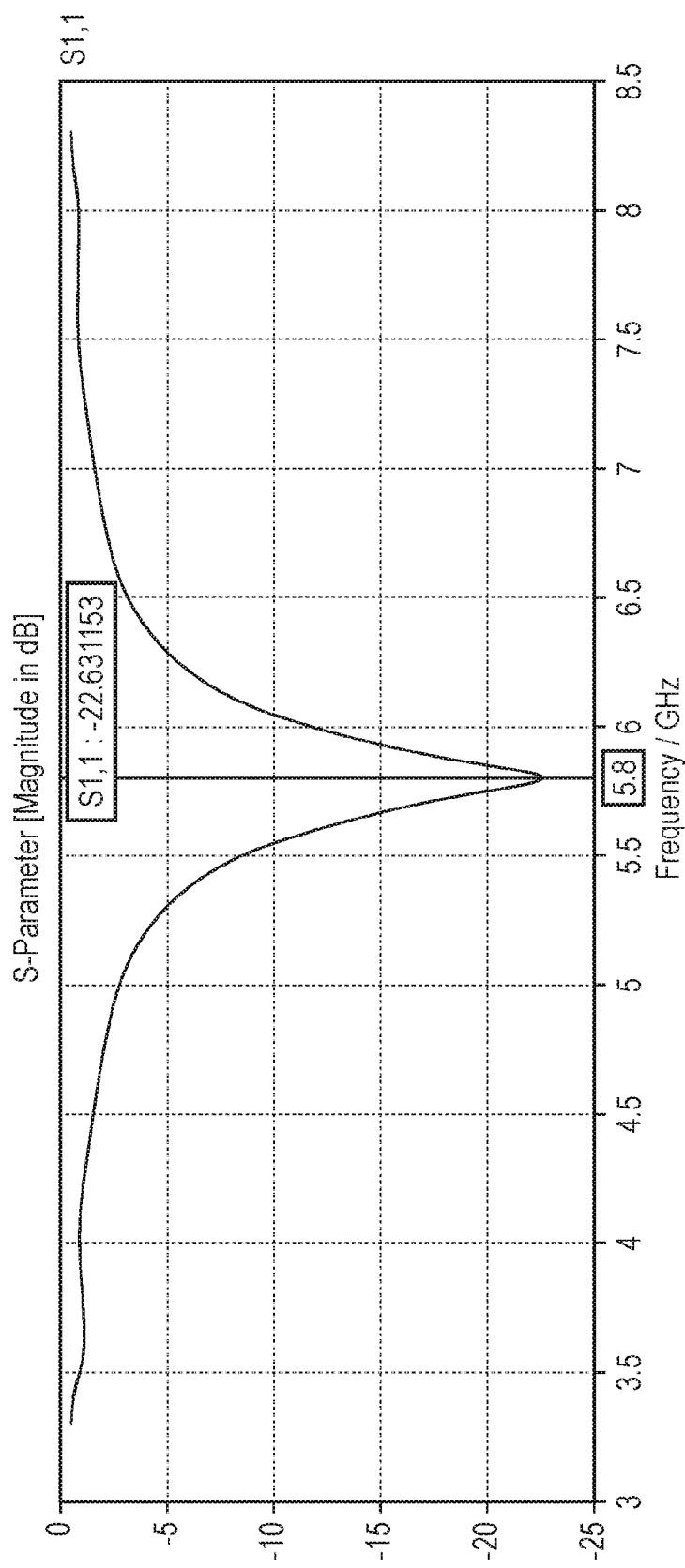
FIG. 2 is a plot of the magnitude of the S-parameter (return loss) against the frequency of the microwave radiation for the computer simulation shown in FIG. 1.

FIG. 2 is a plot of the magnitude of the S-parameter (return loss) against the frequency of the microwave radiation for the computer simulation shown in FIG. 1. As well known in the technical field, the S-parameter is a measure of the return loss of microwave energy due to impedance mismatch, and as such the S-parameter is indicative of the degree of impedance mismatch. The S-parameter can be defined by equation (6).

$$P_I = SP_R \tag{6}$$

where $P_I$ is the outgoing power in the instrument towards the tissue, $P_R$ is the reflected power away from the tissue and S is the S-parameter.

As shown in FIG. 2, in the simulation results there is a very good impedance match for the desired operating frequency of 5.8 GHz, meaning very little microwave energy was reflected away from the liver tissue at this frequency of microwave energy in the simulations. This demonstrates that configuring the length and diameter parameters of the distal coaxial transmission line of the electrosurgical instrument as discussed above can maximise the amount of microwave energy that is delivered by the electrosurgical instrument into the desired localised area of tissue in contact with the distal end of the distal coaxial transmission line.

While such a good match may be difficult to achieve in practice, these results also illustrate that an acceptable match of the impedances may be achievable over a range of different tissues with different (but similar) relative permittivities. For example, a poorer but still acceptable S-parameter of −15 dB may be achieved with a different type of tissue having a slightly higher or lower impedance than liver tissue.

Further simulations were carried out to determine the effect of tilting the instrument so that only the corner of the distal end of the distal coaxial transmission line was in contact with the tissue. It was found that for angles greater than 1 degree between the distal end of the distal coaxial transmission line and the surface of the tissue the match was poor. The simulated absorption pattern for 5 degrees tilt is shown in FIG. 3 and the S-parameter (return loss) for 1, 2 and 5 degrees tilt is shown in FIG. 4.

Figure 3:
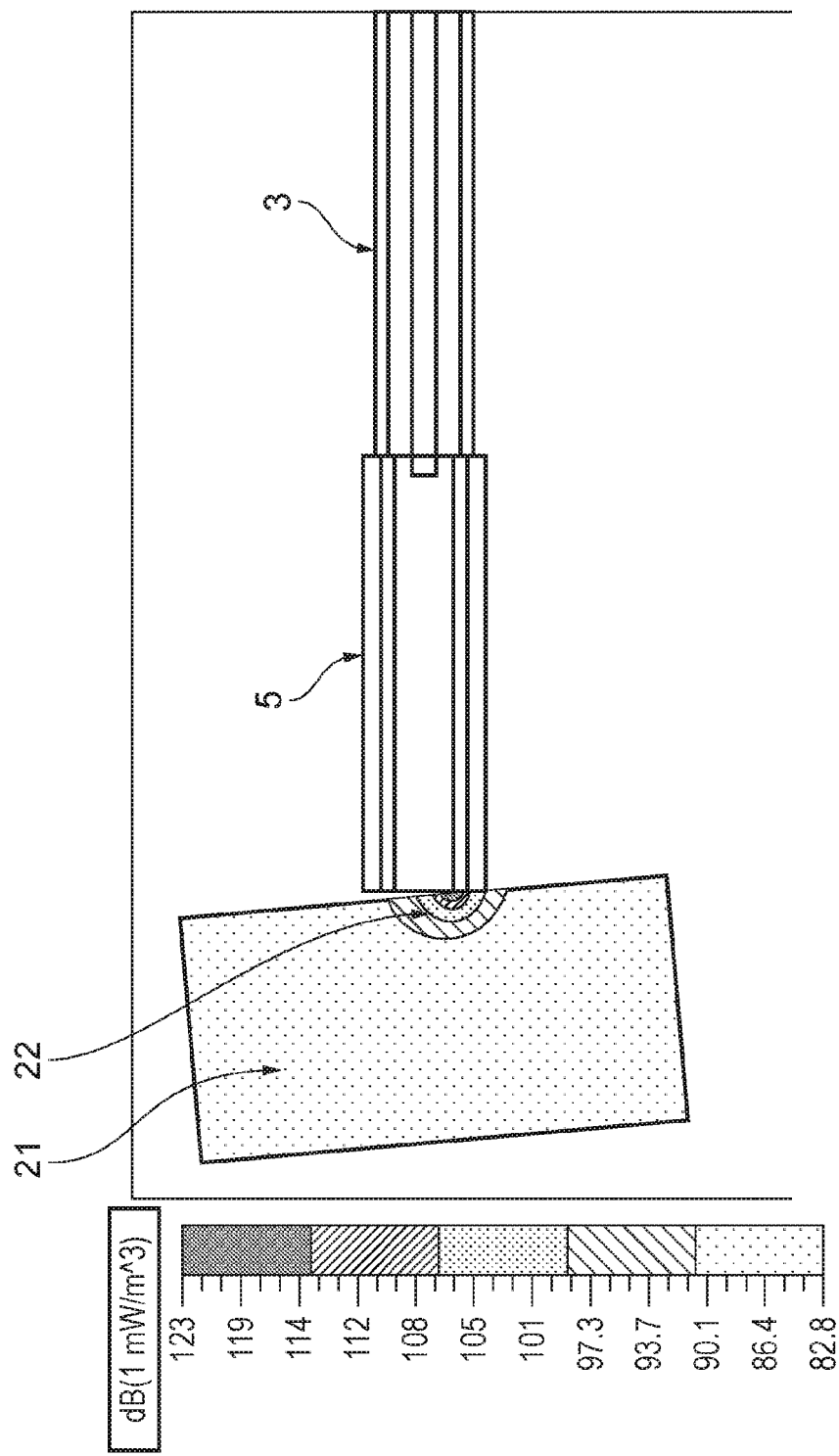
FIG. 3 shows a further computer simulation of an electrosurgical instrument according to an embodiment of the present invention being used to coagulate liver tissue with the instrument at an angle to the normal of the liver tissue surface.

As shown in FIG. 3, when the electrosurgical instrument is tilted so that only part of the electrosurgical instrument contacts the tissue, the microwave power is delivered into an even smaller localised area of tissue where the contact is made. As shown in FIG. 3, the power delivery pattern 22 is smaller and more localised than the power delivery pattern 19 in FIG. 1.

For 5 degrees tilt the power radiated, i.e. that left the electrosurgical instrument but did not enter the intended tissue, was −23.18 dB compared to the input power, i.e. about 0.5%. The return loss was −0.84 dB, i.e. only about 17.5% of the power left the applied end of the electrosurgical instrument, and about 97% of this power was absorbed in the intended tissue.

Figure 4:
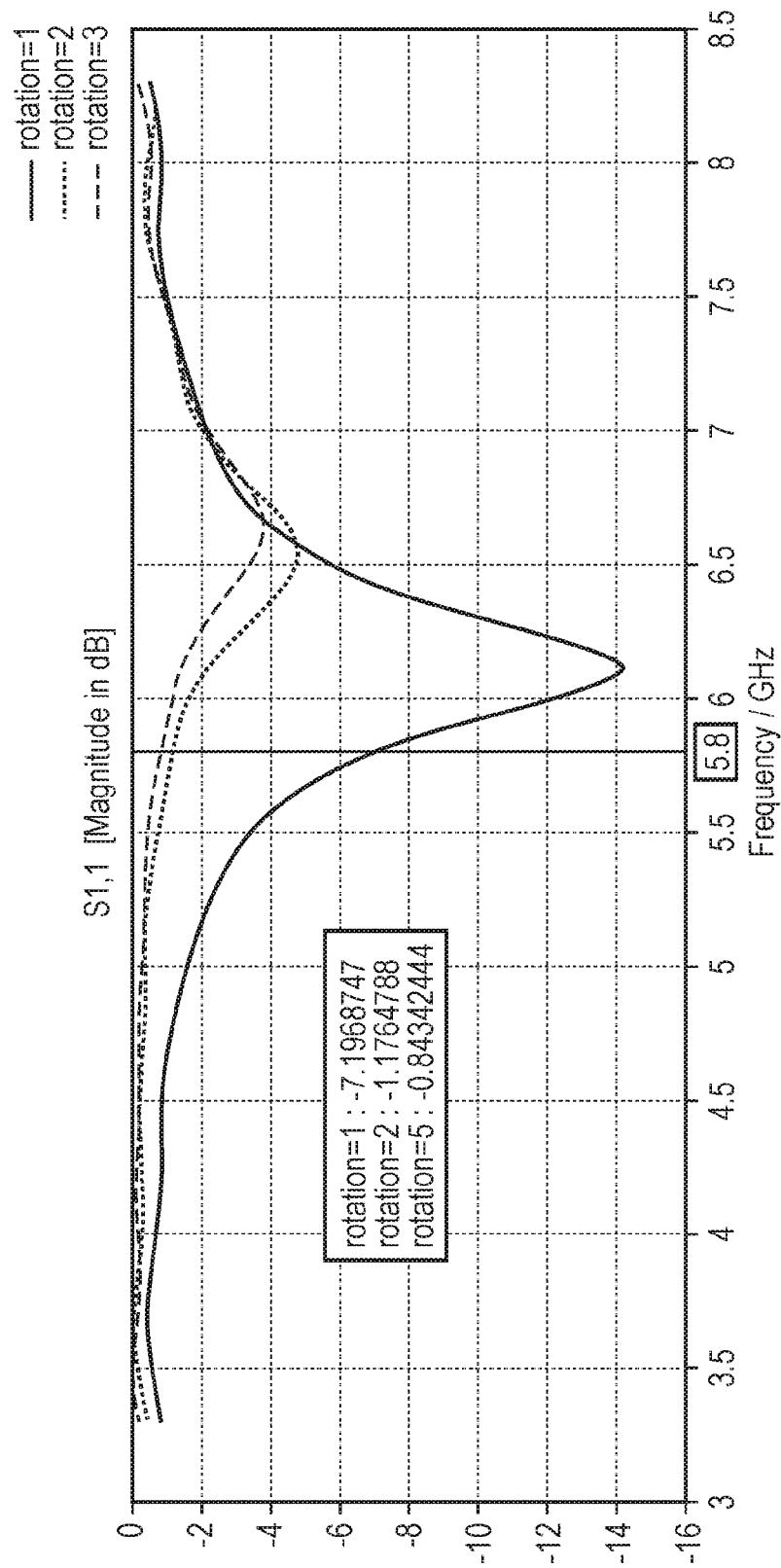
FIG. 4 is a plot of the magnitude of the S-parameter (return loss) against the frequency of the microwave radiation for the further computer simulation shown in FIG. 3 for three different angles of the instrument.

As shown in FIG. 4, increasing the amount of the angle/tilt between the central axis of the instrument and the normal to the tissue surface significantly increases the return loss, meaning more of the microwave power is reflected and less of the microwave power is delivered to the tissue. The electrosurgical instrument will therefore be less efficient at these higher angles of tilt, but the microwave energy will be localised into a smaller area.

Figure 5:
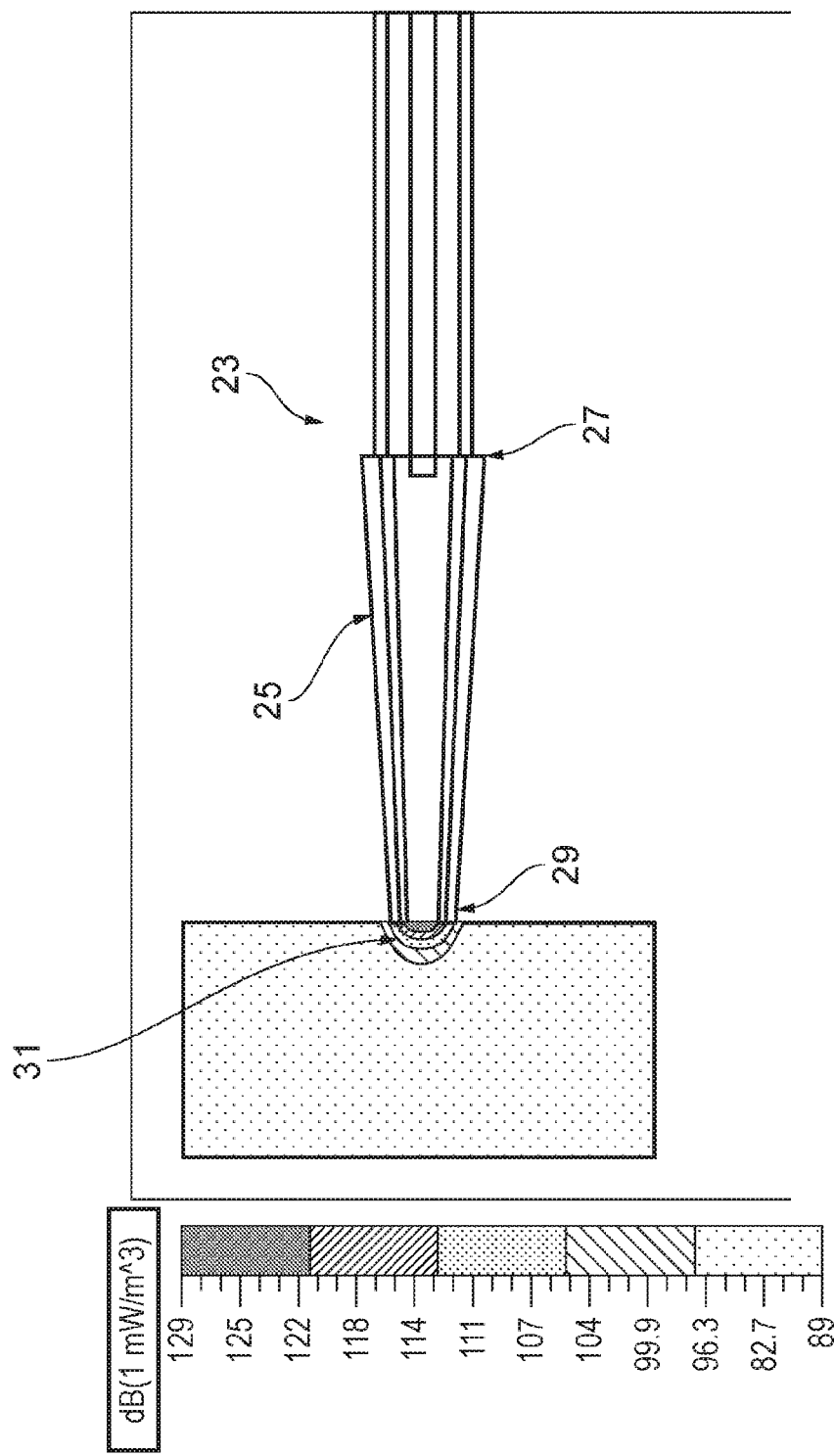
FIG. 5 shows a computer simulation of an electrosurgical instrument according to a further embodiment of the present invention being used to coagulate liver tissue.

FIG. 5 shows a computer simulation result for an electrosurgical instrument 23 according to a second embodiment of the present invention. The electrosurgical instrument 23 according to the second embodiment differs from the electrosurgical instrument 1 according to the first embodiment because in the second embodiment the second coaxial transmission line 25 tapers from a wider proximal end 27 to a narrower distal end 29. In this embodiment the distal end 29 has approximately half the diameter of the proximal end 27.

Specifically, in this embodiment at the distal end 29 of the second coaxial transmission line the diameter of the second inner conductor is 0.6 mm, the diameter of the second dielectric layer is 0.9 mm and the outer diameter of the second outer conductor is 1.25 mm.

In this embodiment the ratio of the inner diameter of the outer conductor to the outer diameter of the inner conductor is kept constant along the length of the distal coaxial transmission line, so that the impedance of the distal coaxial transmission line is constant along its length. Furthermore, the proportions of the exposed distal end of the distal coaxial transmission line that is in contact with the tissue is the same as in the embodiment of FIG. 1.

As shown in FIG. 5, an advantage of the second coaxial transmission line 25 being tapered in this manner is that the microwave energy is delivered to a smaller area of the tissue at the distal end of the second coaxial transmission line 25. This can be seen by comparing the power absorption pattern 19 in FIG. 1 with the power absorption pattern 31 in FIG. 5. Thus, the microwave energy delivery is more localised in the second embodiment. This may be particularly useful, for example, when it is desirable to focus the energy delivery into a specific area or type of tissue, for example into a blood vessel or lumen.

Figure 6:
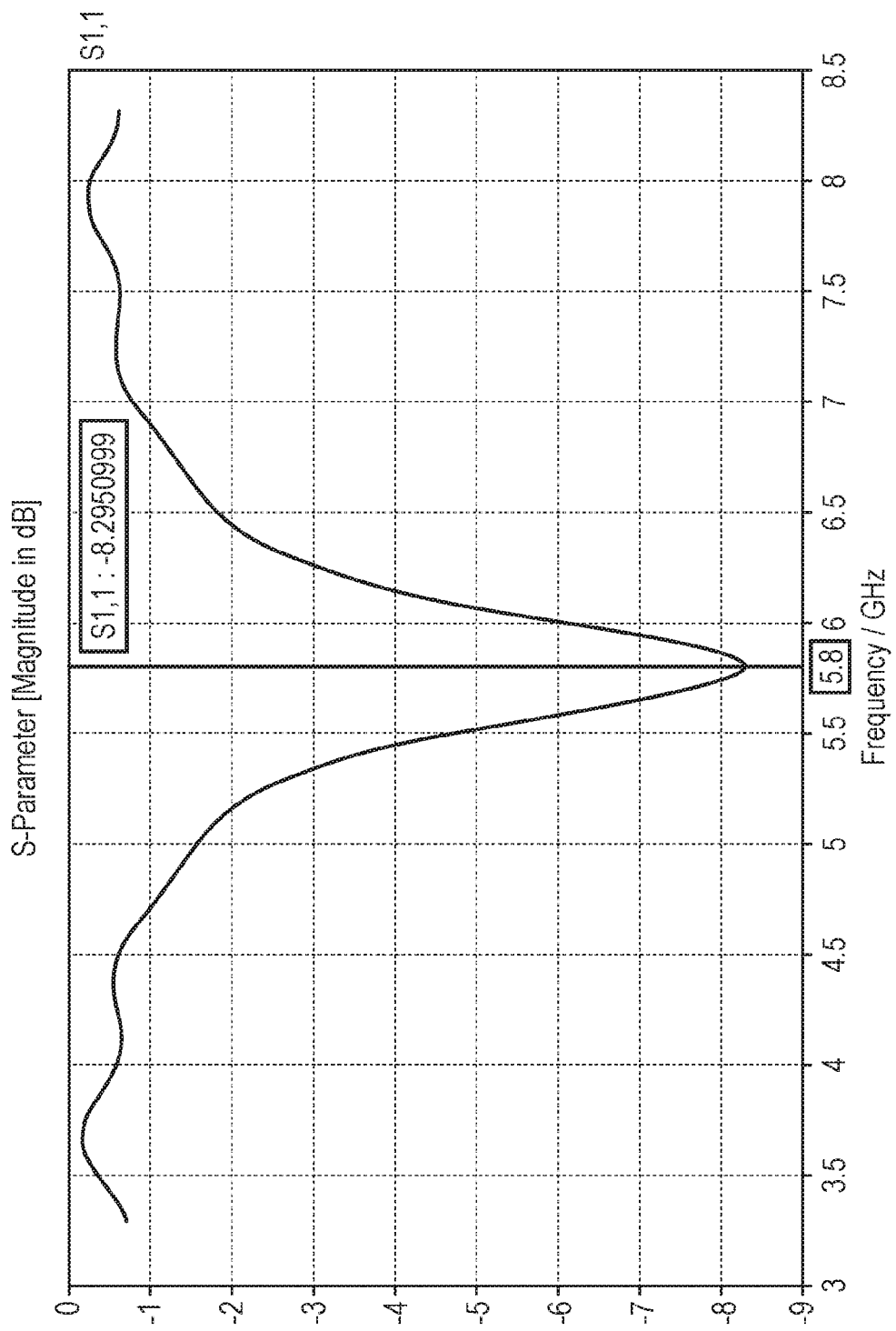
FIG. 6 is a plot of the magnitude of the S-parameter (return loss) against the frequency of the microwave radiation for the computer simulation shown in FIG. 5

FIG. 6 is a plot of the magnitude of the S-parameter (return loss) against the frequency of the microwave radiation for the computer simulation shown in FIG. 5. In this simulation the length of the second coaxial transmission line 25 was lengthened from the 9 mm of the first embodiment to 10 mm so that the lowest return loss was obtained at the desired operating frequency of 5.8 GHz. The change in length of the second coaxial transmission line was necessary because the wavelength of the microwave frequency energy is longer with this tapered geometry of the second coaxial transmission line (this is an example in which the optimal length of the second coaxial transmission line is not an odd multiple of $\lambda/4$.

It is apparent from FIG. 6 that the return loss is more significant than with the embodiment illustrated in FIG. 1 (compare FIGS. 6 and 2). This may be because the geometry (e.g. length and ratio of the diameters) of the second coaxial transmission line was not fully optimised for the liver load tissue. Therefore, it may be possible to achieve a lower return loss with this geometry of the second coaxial transmission line by further optimising the geometry of the second coaxial transmission line.

However, the performance of the instrument 25 is still good with this return loss so the instrument 25 can be successfully used to coagulate the tissue, and as discussed above this embodiment has an advantage that the power is delivered into a smaller volume of tissue.

A further advantage of the tapered nature of the second coaxial transmission line 25 in this embodiment is that it is possible to press the distal end of the coaxial transmission line 25 further into the tissue than with the first embodiment, because the distal tip is narrower in this embodiment.

The other features of the second embodiment are the same as in the first embodiment and description thereof is not repeated here for conciseness.

Delivery of the microwave frequency energy into a more localised area of the tissue may also be achieved by maintaining the cylindrical shape of the second coaxial transmission line shown in FIG. 1 but using a narrower coaxial transmission line. This similarly results in a narrower distal end of the second coaxial transmission line for delivering the microwave frequency energy into a more localised area of tissue.

Figure 7:
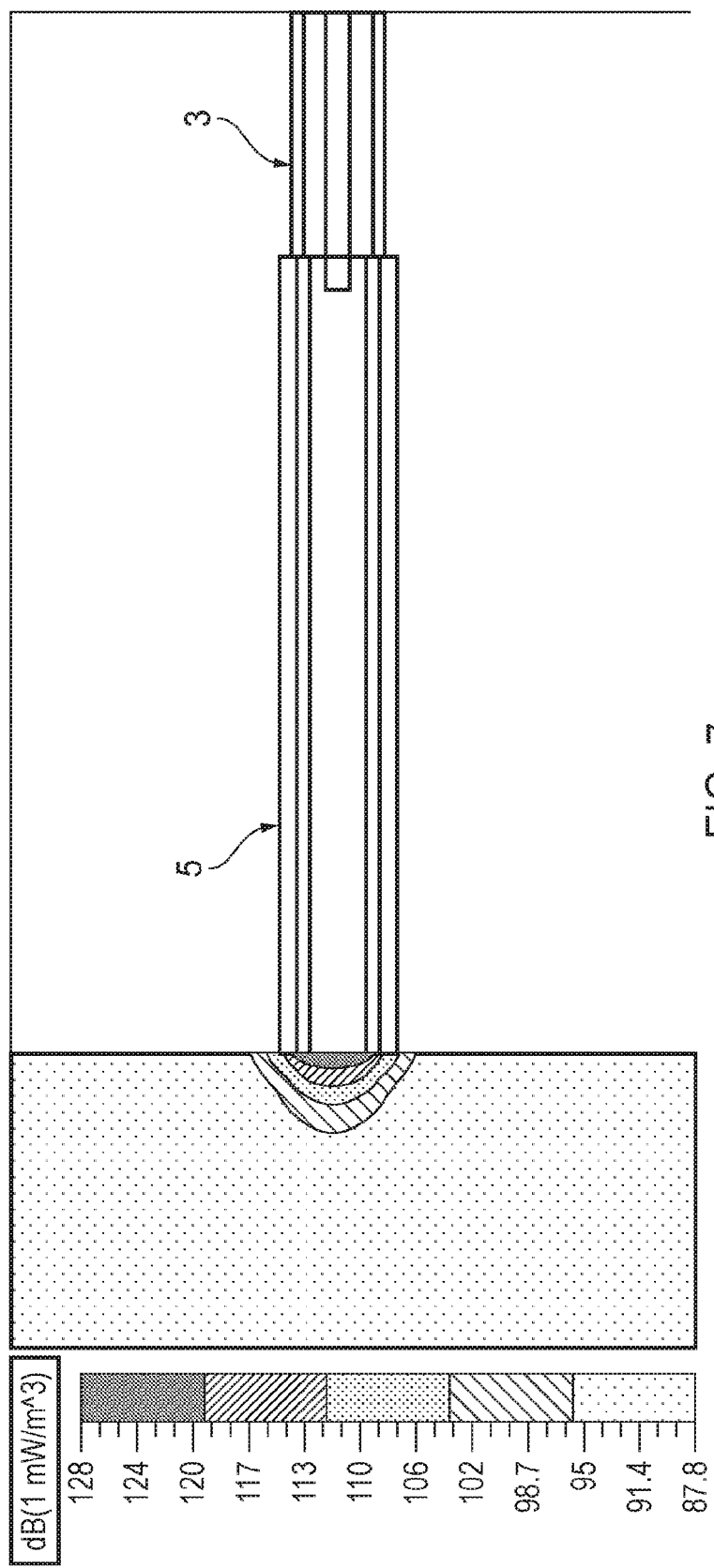
FIG. 7 shows a computer simulation of an electrosurgical instrument according to a further embodiment of the present invention being used to coagulate liver tissue, wherein the first and second coaxial transmission lines are narrower than in the embodiment of FIG. 1.

FIG. 7 shows a computer simulation of an electrosurgical instrument according to a further embodiment of the present invention being used to coagulate liver tissue, wherein the first and second coaxial transmission lines are narrower than in the embodiment of FIG. 1. The configuration of the instrument shown in FIG. 7 is similar to that shown in FIG. 1 apart from the dimensions of the first and second coaxial transmission lines. Only the differences from the embodiment shown in FIG. 1 will be discussed here.

In the embodiment of FIG. 7, the first coaxial transmission line is Sucoform 47 coaxial cable. Sucoform 47 coaxial cable comprises the same materials as Sucoform 86 coaxial cable discussed above, but different dimensions. Specifically, in Sucoform 47 cable the inner conductor has an outer diameter of 0.31 mm, the PTFE dielectric layer has an outer diameter of 0.94 mm and the outer conductor has an outer diameter of 1.20 mm. Sucoform 47 cable has a characteristic impedance of 50 Ohms.

A potential disadvantage of using Sucoform 47 as the first coaxial transmission line relative to the wider Sucoform 86 cable is that the Sucoform 47 cable has higher losses, so the efficiency of the instrument will be lower. However, an advantage of using Sucoform 47 is that the relative proportions of the first and second coaxial transmission lines at the junction between them are similar to the previously described embodiments, despite the diameter of the second coaxial transmission line being narrower.

The second coaxial transmission line is a cylindrical transmission line that is narrower than in FIG. 1. Specifically, the second inner conductor has an outer diameter of 0.702 mm, the second dielectric layer has an outer diameter of 1.053 mm and the second outer conductor has an outer diameter of 1.462 mm.

As shown in FIG. 7, the narrower nature of the second coaxial transmission line 5 in this embodiment results in more localised delivery of the microwave frequency energy into the liver tissue (compare FIGS. 1 and 7, taking into account the different scales).

Figure 8:
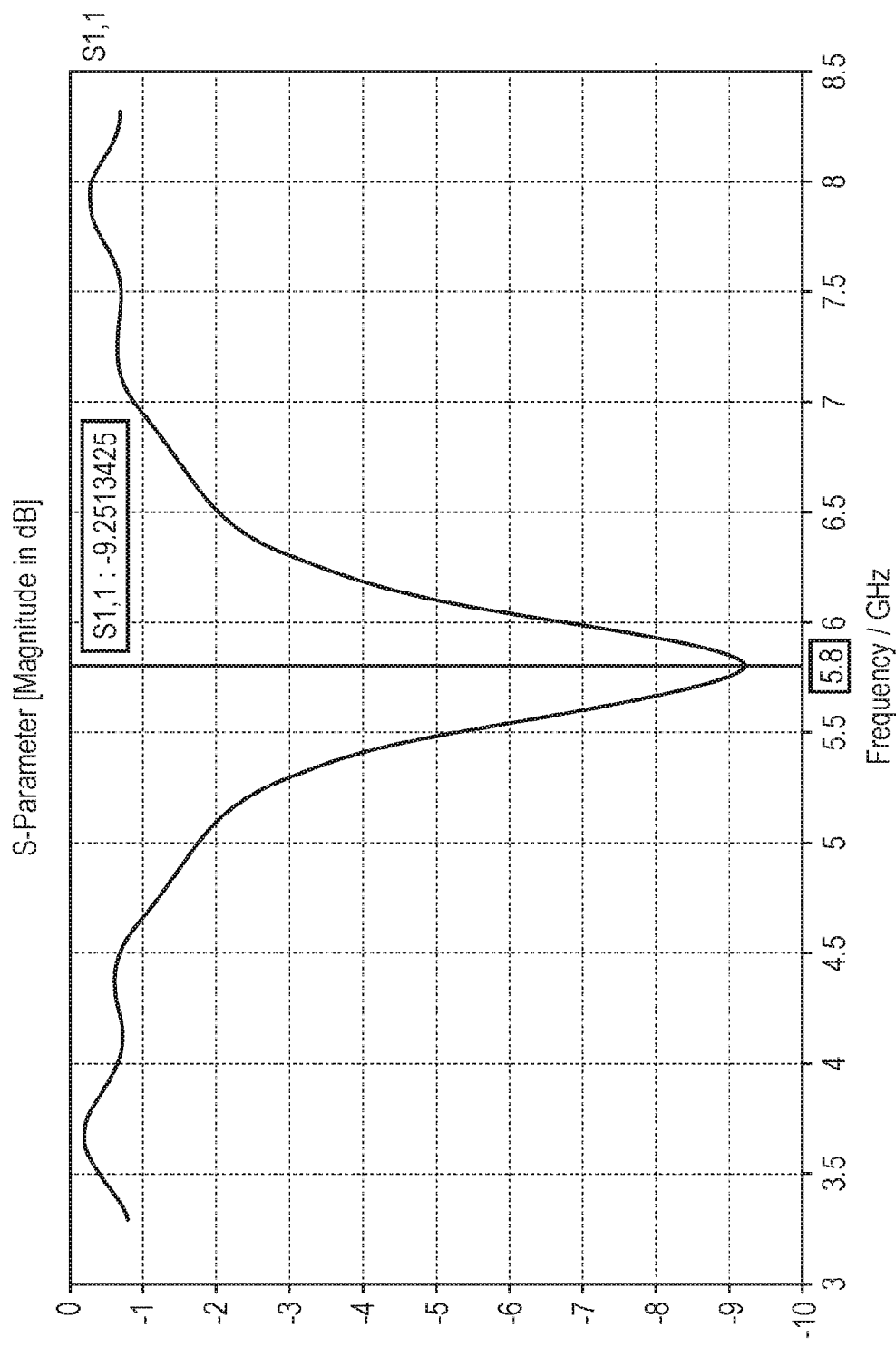
FIG. 8 is a plot of the magnitude of the S-parameter (return loss) against the frequency of the microwave radiation for the computer simulation shown in FIG. 7.

FIG. 8 is a plot of the magnitude of the S-parameter (return loss) against the frequency of the microwave radiation for the computer simulation shown in FIG. 7. As can be seen by comparing FIGS. 6 and 8, the return loss for this embodiment is comparable to the return loss of the tapered embodiment illustrated in FIG. 5.

Figure 9:
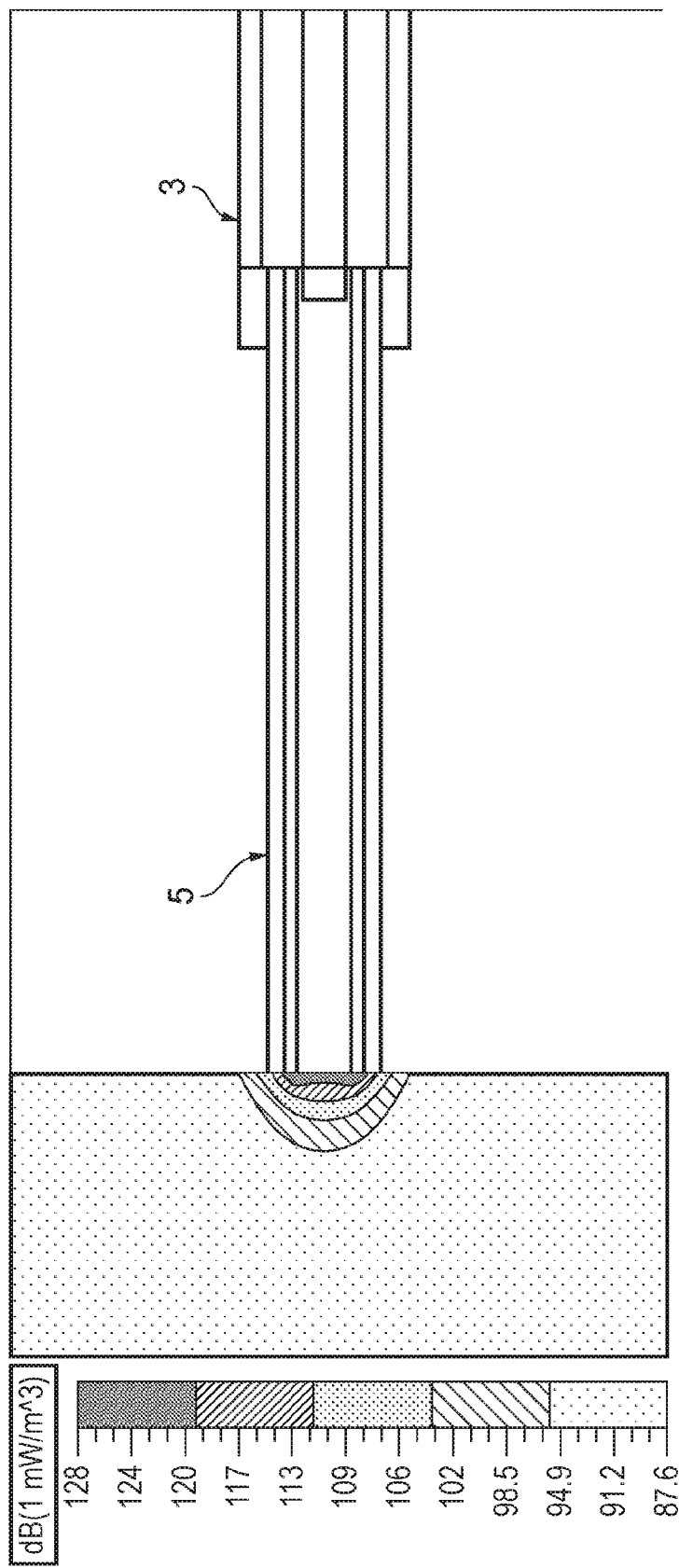
FIG. 9 shows a computer simulation of an electrosurgical instrument according to a further embodiment of the present invention being used to coagulate liver tissue, wherein the second coaxial transmission line is narrower than in the embodiment of FIG. 1.
Figure 10:
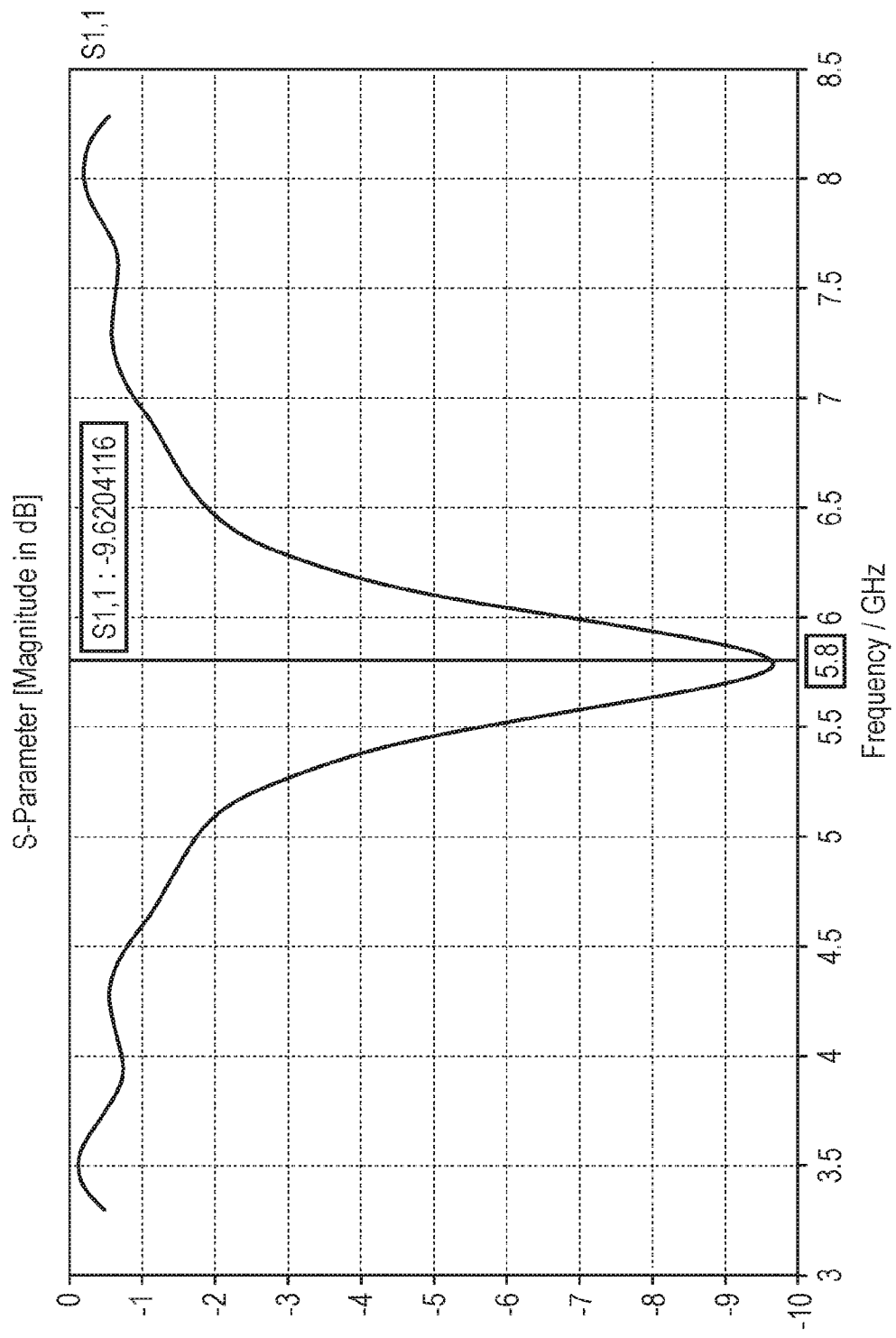
FIG. 10 is a plot of the magnitude of the S-parameter (return loss) against the frequency of the microwave radiation for the computer simulation shown in FIG. 9.

FIG. 9 shows a computer simulation of an electrosurgical instrument according to a further embodiment of the present invention being used to coagulate liver tissue, wherein the second coaxial transmission line is narrower than in the embodiment of FIG. 1. FIG. 10 is a plot of the magnitude of the S-parameter (return loss) against the frequency of the microwave radiation for the computer simulation shown in FIG. 9.

The configuration of the instrument shown in FIG. 9 is similar to that shown in FIG. 1 apart from the dimensions of the second coaxial transmission line. Only the differences from the embodiment shown in FIG. 1 will be discussed here.

The first coaxial transmission line in the embodiment shown in FIG. 9 is Sucoform 86 coaxial cable, as in the embodiment of FIG. 1. However, the second coaxial transmission line is narrower, and has the same dimensions as in the embodiment of FIG. 7. In other words, the second inner conductor has an outer diameter of 0.702 mm, the second dielectric layer has an outer diameter of 1.053 mm and the second outer conductor has an outer diameter of 1.462 mm. As shown in FIG. 9, more localised delivery of the microwave frequency energy into the tissue can be achieved with the embodiment of FIG. 9 than with the embodiment of FIG. 1, because of the narrower distal tip of the second coaxial transmission line in FIG. 9.

FIG. 10 shows that the return loss is acceptable when feeding the second coaxial transmission line using the wider Sucoform 86 cable instead of the narrower Sucoform 47 cable.

An advantage of using the wider Sucoform 86 coaxial cable as the first coaxial transmission line is that the power loss is less in this cable. Therefore, the efficiency of the instrument will be greater when Sucoform 86 cable is used as the first coaxial transmission line.

The dimensions of the distal tip of the second coaxial feed cables in FIGS. 1, 5, 7 and 9 are set out in Table 1 below, for ease of reference.

TABLE 1

| Embodiment | Inner conductor diameter | Dielectric layer diameter | Outer conductor diameter |
|---|---|---|---|
| FIG. 1 | 1.2 mm | 1.8 mm | 2.5 mm |
| FIG. 5 | 0.6 mm | 0.9 mm | 1.25 mm |
| FIGS. 7 and 9 | 0.702 mm | 1.053 mm | 1.462 mm |

Of course, in alternative embodiments the dimensions may be different to those given in Table 1.

In summary, all embodiments of the present invention provide an electrosurgical instrument that efficiently couples microwave energy into a localised area of tissue directly in contact with the electrosurgical instrument.

The delivery of the microwave energy to the tissue is significantly improved where good contact is made between the distal end of the electrosurgical instrument (for example the distal end of the second coaxial transmission line) and the tissue. Where the electrosurgical instrument is at an angle so that there is an air gap between at least part of the distal end of the electrosurgical instrument and the tissue the return loss can be poor, particularly for angles of greater than 1 degree.

In all embodiments, very little power is radiated in unwanted directions (in other words in any direction other than into the area of tissue in contact with the probe), regardless of the return loss.

In all embodiments the electrosurgical instrument can be used to contact the tissue at an angle to coagulate a very small piece of tissue close to the edge of the distal end of the second coaxial transmission line.

In addition, a more concentrated region of heating of the tissue may also be achieved by using a tapered second coaxial transmission line to deliver the microwave energy into a smaller area of tissue at the distal end of the second coaxial transmission line.

More concentrated delivery of microwave frequency energy into the tissue can also be achieved by using a narrower cylindrical second coaxial transmission line. In order to reduce power losses, the narrower second coaxial transmission line may be fed by a wider first coaxial transmission line.

Figure 11:
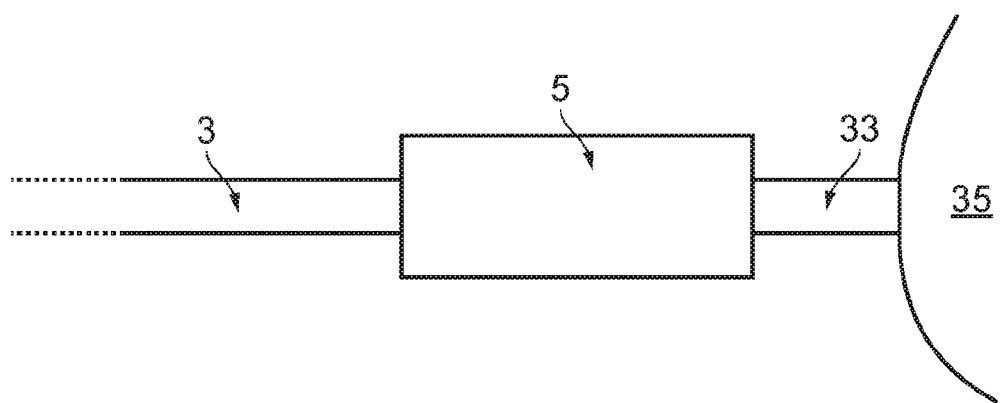
FIG. 11 is a schematic illustration of an electrosurgical instrument according to a further embodiment of the present invention.

FIG. 11 is a schematic illustration of a further embodiment of the present invention. As with the previously described embodiments, in this embodiment the electrosurgical instrument comprises the first and second coaxial transmission lines 3, 5. The configuration of the first and second coaxial transmission lines 3, 5 shown in FIG. 11 is an example configuration only, and the first and second coaxial transmission lines may instead have another configuration (shape, size, etc.), for example one of the other example configurations of the other embodiments described above and illustrated in FIGS. 1 to 10.

In this embodiment the electrosurgical instrument comprises a third coaxial transmission line 33. The third coaxial transmission line 33 comprises a third inner conductor that is connected to the second inner conductor, a third outer conductor that is coaxial with the third inner conductor and connected to the second outer conductor, and a third layer of dielectric material separating the third inner and outer conductors.

The third coaxial transmission line 33 is axially aligned with (coaxial with) the first and second coaxial transmission lines 3, 5.

The third inner conductor, third outer conductor and third layer of dielectric material are exposed at a planar distal end face of the third coaxial transmission line 33. In use, as illustrated in FIG. 11, the distal end face of the third coaxial transmission line 33 can be pressed against tissue to deliver microwave frequency energy into the tissue, as described in more detail below. Thus, in this embodiment the distal end of the third coaxial transmission line 33 forms the distal end of the instrument, and not the distal end of the second coaxial transmission line 5 as in the previously described embodiments.

The third coaxial transmission line 33 is configured to remove a reactive part (imaginary component) of the impedance of the tissue 35. Once the reactive part of the impedance of the tissue 35 has been removed, the second coaxial transmission line 5 matches the subsequent purely real impedance to the impedance of the first coaxial transmission line 3. Thus, the effects of impedance mismatch of both the real and reactive (imaginary) parts of the impedance of the tissue 35 are taken into account and addressed in this embodiment.

In this embodiment the third coaxial transmission line 33 has the same impedance as the first coaxial transmission line 3 (for example 50 Ohm). Indeed, in this embodiment the third coaxial transmission line 33 is a same type of coaxial cable as the first coaxial transmission line 3.

An appropriate length for the third coaxial transmission line 33 to cancel out/remove the reactive part of the impedance of the tissue 35 can be determined mathematically, for example using a Smith Chart, based on variables such as the impedances of the tissue and the first coaxial transmission line and the frequency of the microwave frequency radiation. If the calculated length of the third coaxial transmission line is too short to be practical, a multiple of $\lambda/2$ can be added to the calculated length to determine a more practically appropriate length. The appropriate length of the third coaxial transmission line may alternatively be determined by computer simulation/modelling, or by experimentation.

As an example, the appropriate length of the third coaxial transmission line may be determined using the following steps, assuming the tissue impedance (load) is $(10-j10)\Omega$ and the impedance of the first coaxial transmission line is $50\Omega$:

(1) Normalise the tissue impedance to the impedance of the first coaxial transmission line:

$$Z_N = \frac{(10 - j10)\Omega}{50\Omega} = (0.2 - j0.2)\Omega;$$

(2) Plot the normalised impedance on the Smith Chart and draw the VSWR circle;
(3) Rotate the normalised load to the real r axis and note the movement in wavelengths from the load towards the generator. This removes the reactive (imaginary) component of the impedance of the load;
(4) If the Δλ is too short to realise practically, add $$\frac{n\lambda}{2}$$

to this length until a practical length is achieved.

Once the reactive part of the impedance of the tissue has been cancelled out, the subsequently purely real impedance can be matched to the impedance of the first coaxial transmission line by an appropriately configured second coaxial transmission line. Specifically, the Smith Chart can be used to find the value from the real r axis where the load has a purely real value only (which may be to the left or the right of the centre), and this value can then be normalised by multiplying by the impedance of the first coaxial transmission line to find the real impedance to be matched to the impedance of the first coaxial transmission line.

The following is a simple numerical example relating to the embodiment of FIG. 11, assuming the tissue impedance (load) is $(10-j10)\Omega$ and the impedance of the first coaxial transmission line is $50\Omega$.

Carrying out the above steps using a Smith Chart results in the desired length of the third coaxial transmission line being determined to be $0.033\lambda$ and the value from the real r axis where the load has a purely real value only to be $r_{new}=0.19$. The normalised load to be matched to the impedance of the first coaxial transmission line 3 by the second coaxial transmission line 5 is then determined to be $Z_{new}=0.19\times50\Omega=9.5\Omega$. The optimal impedance of the second coaxial transmission line 5 can thus be determined to be:

$$Z_T=\sqrt{Z_{in}Z_L}=\sqrt{50\times 9.5}=21.8\Omega$$

Appropriate diameters for the second inner and outer conductors can then be determined based on this value and equation (6).

Assuming a microwave frequency of 5.8 GHz and that the second dielectric material is PTFE with a relative permittivity of 1.5, the optimal length of the second coaxial transmission line 5, i.e.

$$\frac{\lambda}{4},$$

can be determined using equation (3) to be 10.56 mm. If this length is too short to be practical, it can be increased by adding a multiple of $$\frac{\lambda}{2}$$

to the length, for to arrive at a length of 31.68 mm.

As mentioned above, the desired length of the third coaxial transmission line 33 in this example is $0.033\Omega$, which corresponds to a length of 1.39 mm. Again, if this length is too short to be practical, it can be increased by adding a multiple of $$\frac{\lambda}{2}$$

to the length, for to arrive at a length of 22.51 mm.

The following is a simple numerical example illustrating the need for impedance matching in the embodiments of the present invention. This example assumes a tissue impedance of $(12-j15)\Omega$ and a single coaxial transmission line with an impedance of $50\Omega$ pressed against the tissue.

Without any impedance matching the amount of power that would be reflected would be:

$$\Gamma = \frac{Z_L - Z_0}{Z_L + Z_0} = 0.63 - j0.37$$

$$|\Gamma| = 0.731$$

The proportion of power delivered to the tissue load is then given by:

$$P=(1-0.731^2)=0.466$$

Thus, with no impedance matching only 47% of the power will be delivered to the load, which means that the electrosurgical instrument would be relatively inefficient. The delivered power can be significantly improved by performing impedance matching as in the embodiments of the present invention described above.

In one practical embodiment, the dielectric material in the second and/or third coaxial transmission line may be air, or another gas. In this case, a piece of material may be positioned over the end of the coaxial transmission line, for example a piece of Kepton tape or a mica window.

The invention claimed is:

1. An electrosurgical instrument configured for delivering microwave frequency energy having a predetermined operating frequency into tissue having a predetermined characteristic impedance in contact with a distal end of the instrument, the instrument comprising:
   a proximal coaxial transmission line for conveying microwave frequency energy comprising a first inner conductor, a first outer conductor formed coaxially with the first inner conductor, and a first dielectric layer separating the first inner conductor and the first outer conductor;
   a distal coaxial transmission line for conveying microwave frequency energy comprising a second inner conductor connected to the first inner conductor, a second outer conductor formed coaxially with the second inner conductor and connected to the first outer conductor, and a second dielectric layer separating the second inner conductor and the second outer conductor;
   wherein a ratio of an inner diameter of the second outer conductor to the outer diameter of the second inner conductor is such that a characteristic impedance of the distal coaxial transmission line is intermediate between a characteristic impedance of the proximal coaxial transmission line and a load impedance at the distal end of the distal coaxial transmission line when the distal end of the instrument is in contact with the tissue;
   wherein a length of the distal coaxial transmission line is such that the distal coaxial transmission line is an impedance transformer that improves the impedance match between the proximal coaxial transmission line and the load impedance at the distal end of the distal coaxial transmission line when the distal end of instrument is in contact with the tissue, at the predetermined operating frequency; and wherein the electrosurgical instrument comprises a further distal coaxial transmission line comprising a third inner conductor connected to the second inner conductor, a third outer conductor formed coaxially with the third inner conductor and connected to the second outer conductor, and a third dielectric layer separating the third inner conductor and the third outer conductor.

2. The electrosurgical instrument according to claim 1, wherein a length of the distal coaxial transmission line is substantially equal to $(2n+1)\lambda/4$, where $\lambda$ is the wavelength in the distal coaxial transmission line of microwave frequency energy having the predetermined operating frequency and n is an integer greater than or equal to 0.

3. The electrosurgical instrument according to claim 1, wherein the electrosurgical instrument is for coagulating tissue.

4. The electrosurgical instrument according to claim 1, wherein the ratio of the inner diameter of the second outer conductor to the outer diameter of the second inner conductor is such that a characteristic impedance of the distal coaxial transmission line is substantially equal to $\sqrt{Z_{in}Z_L}$, where $Z_{in}$ is the characteristic impedance of the proximal coaxial transmission line and $Z_L$ is the load impedance at the distal end of the distal coaxial transmission line when the distal end of the instrument is in contact with the tissue.

5. The electrosurgical instrument according to claim 1, wherein a characteristic impedance of the further distal coaxial transmission line is the same as a characteristic impedance of the proximal coaxial transmission line.

6. The electrosurgical instrument according to claim 1, wherein a length of the further distal coaxial transmission line is such that the further distal coaxial transmission line substantially cancels out a reactive part of the predetermined characteristic impedance of the tissue at the predetermined operating frequency.

7. The electrosurgical instrument according to claim 1, wherein the further distal coaxial transmission line is rigid.

8. The electrosurgical instrument according to claim 1, wherein the electrosurgical instrument comprises:

an open-circuited or short-circuited stub connected in parallel to the further distal coaxial transmission line.

9. The electrosurgical instrument according to claim 8, wherein a characteristic impedance of the stub is the same as a characteristic impedance of the further distal coaxial transmission line.

10. The electrosurgical instrument according to claim 8, wherein a characteristic impedance of the stub is not the same as a characteristic impedance of the further distal coaxial transmission line.

11. The electrosurgical instrument according to claim 8, wherein the electrosurgical instrument comprises a plurality of the open-circuited or short-circuited stubs connected in parallel to the further distal coaxial transmission line.

12. The electrosurgical instrument according to claim 1, wherein a separation between the outer diameter of the second inner conductor and the inner diameter of the second outer conductor is less than a separation between an outer diameter of the first inner conductor and an inner diameter of the first outer conductor.

13. The electrosurgical instrument according to claim 1, wherein the second dielectric layer has a higher relative permittivity than the first dielectric layer.

14. The electrosurgical instrument according to claim 1, wherein the distal coaxial transmission line is rigid.

15. The electrosurgical instrument according to claim 1, wherein the distal coaxial transmission is tapered from a wider proximal end thereof to a narrower distal end thereof.

16. The electrosurgical instrument according to claim 1, wherein the proximal coaxial transmission line is a coaxial cable.

17. The electrosurgical instrument according to claim 1, wherein the electrosurgical instrument comprises a plurality of the distal coaxial transmission lines connected in series between the proximal coaxial transmission line and the further distal coaxial transmission line, each of the plurality of distal coaxial transmission lines being configured to improve the impedance match between the proximal coaxial transmission line and the tissue at the predetermined operating frequency.

* * * * *